(12) United States Patent
Jeon et al.

(10) Patent No.: US 10,767,302 B2
(45) Date of Patent: Sep. 8, 2020

(54) BATHROOM MANAGEMENT APPARATUS

(71) Applicant: LG ELECTRONICS INC., Seoul (KR)

(72) Inventors: Jinhyeon Jeon, Seoul (KR); Jeongyun Kim, Seoul (KR); Daeyun Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 250 days.

(21) Appl. No.: 15/913,257

(22) Filed: Mar. 6, 2018

(65) Prior Publication Data
US 2018/0251932 A1    Sep. 6, 2018

(30) Foreign Application Priority Data
Mar. 6, 2017  (KR) .................... 10-2017-0028492

(51) Int. Cl.
*D06F 58/10*  (2006.01)
*A47B 55/00*  (2006.01)
(Continued)

(52) U.S. Cl.
CPC .......... *D06F 58/10* (2013.01); *A47B 47/0091* (2013.01); *A47B 47/042* (2013.01);
(Continued)

(58) Field of Classification Search
CPC ......... A47B 81/00; A47B 96/04; A47B 55/00; A47B 47/0091; A47B 67/005;
(Continued)

(56) References Cited

U.S. PATENT DOCUMENTS 1,941,126 A * 12/1933 Blackman .............. A47B 67/02
                                                       312/329
2,419,226 A *  4/1947 Palmer .................... D06F 57/12
                                                       34/197
(Continued)

OTHER PUBLICATIONS

U.S. Office Action dated Sep. 18, 2019 issued in U.S. Appl. No. 15/913,154.
(Continued)

*Primary Examiner* — Edelmira Bosques
*Assistant Examiner* — Bao D Nguyen
(74) *Attorney, Agent, or Firm* — KED & Associates, LLP

(57) ABSTRACT

Disclosed is a bathroom management apparatus including a cabinet, a frame provided at an inner side of the cabinet to reinforce stiffness of the cabinet, and having a lower side that is spaced apart from a bottom of the cabinet, a function module including at least one of a towel care module, a sterilizing module, a lock box module, a refrigerating module, and a charging module, and mounted inside the frame, a dryer coupled with the function module and disposed inside the frame, and a vane assembly disposed between the cabinet and a lower side of the frame. A first air outlet is provided for airflow in a forward direction, and a second air outlet provided for airflow in a downward direction. The vane assembly may switch a direction of the airflow received from the dryer through the first air outlet and the second air outlet.

18 Claims, 15 Drawing Sheets

(51) Int. Cl.

| | | |
|---|---|---|
| A47B 47/00 | (2006.01) | |
| A47K 10/48 | (2006.01) | |
| F24H 3/02 | (2006.01) | |
| A61L 2/26 | (2006.01) | |
| A61L 2/10 | (2006.01) | |
| A47B 67/00 | (2006.01) | |
| A47B 81/00 | (2006.01) | |
| A47B 96/04 | (2006.01) | |
| A47B 47/04 | (2006.01) | |
| A47B 96/20 | (2006.01) | |
| A47B 95/00 | (2006.01) | |
| F25D 11/00 | (2006.01) | |
| H02J 7/00 | (2006.01) | |

(52) U.S. Cl.
CPC ............ *A47B 55/00* (2013.01); *A47B 67/005* (2013.01); *A47B 81/00* (2013.01); *A47B 96/04* (2013.01); *A47K 10/48* (2013.01); *A61L 2/10* (2013.01); *A61L 2/26* (2013.01); *F24H 3/022* (2013.01); *A47B 95/008* (2013.01); *A47B 96/20* (2013.01); *A47B 2096/208* (2013.01); *A47B 2220/0091* (2013.01); *A61L 2202/11* (2013.01); *F25D 11/00* (2013.01); *H02J 7/0042* (2013.01)

(58) Field of Classification Search
CPC .......... A47B 47/042; A47B 2220/0091; A47B 96/20; A47B 2096/208; A47B 95/008; D06F 58/10; A47K 10/48; F24H 3/022; F25D 11/00; H02J 7/0042; A61L 2/10; A61L 2/26; F26B 25/06; F26B 25/08; F26B 25/14; B65D 88/74; F24F 1/027; F24F 1/028; F24F 1/029; F24F 13/26
USPC ..... 34/231, 90; 312/224, 245; 454/201, 206, 454/208, 292, 293
See application file for complete search history.

(56) References Cited

U.S. PATENT DOCUMENTS

| | | | | |
|---|---|---|---|---|
| 2,598,917 | A * | 6/1952 | Ingram | F25D 17/04 62/417 |
| 3,054,194 | A * | 9/1962 | Hayes | D06F 58/14 34/665 |
| 3,306,689 | A | 2/1967 | Anson | |
| 3,515,450 | A * | 6/1970 | Jaecke | A47B 47/0075 312/245 |
| 3,519,318 | A * | 7/1970 | Hagen | A47B 75/00 312/245 |
| 3,521,936 | A * | 7/1970 | Coker, Jr. | A47B 67/02 312/209 |
| 3,955,922 | A * | 5/1976 | Moulthrop | A61L 2/10 422/300 |
| 4,134,625 | A * | 1/1979 | Palka | A47B 67/005 312/206 |
| 4,189,195 | A * | 2/1980 | Turney | A47B 67/005 312/209 |
| 4,195,416 | A * | 4/1980 | Hall | A47K 10/48 34/233 |
| 4,239,310 | A * | 12/1980 | Benjamin | A47B 67/005 312/224 |
| 4,644,136 | A * | 2/1987 | Watchman | A47K 10/06 219/385 |
| 5,108,162 | A * | 4/1992 | Lund | A47B 67/00 292/213 |
| 5,255,971 | A * | 10/1993 | Aisley | A47B 67/02 312/242 |
| 5,355,627 | A * | 10/1994 | Katz | A47B 81/00 312/227 |
| 5,380,981 | A * | 1/1995 | Feldman | H05B 3/845 219/219 |
| 5,444,984 | A * | 8/1995 | Carson | A47B 81/00 62/3.4 |
| 5,487,877 | A * | 1/1996 | Choi | A47K 5/00 222/192 |
| 5,524,980 | A | 6/1996 | Carter | |
| 5,577,819 | A * | 11/1996 | Olsen | A47B 67/00 312/209 |
| 6,089,685 | A * | 7/2000 | Ryan | A47B 67/04 312/291 |
| 6,365,876 | B1 * | 4/2002 | Park | A47G 1/02 219/219 |
| 6,420,682 | B1 * | 7/2002 | Sellgren | H05B 3/845 156/232 |
| 6,525,298 | B1 | 2/2003 | Hunts | |
| 6,640,581 | B1 * | 11/2003 | Choi | A47B 81/00 62/180 |
| 6,664,513 | B1 * | 12/2003 | Park | H05B 3/845 219/219 |
| 6,769,197 | B1 * | 8/2004 | Tai | A47K 10/48 34/197 |
| 7,083,110 | B2 * | 8/2006 | Kim | E06B 7/10 237/46 |
| 7,258,606 | B1 * | 8/2007 | Reid | F24F 1/027 312/101 |
| 7,543,339 | B1 * | 6/2009 | Harris | E03D 1/01 4/420.5 |
| 8,166,667 | B1 * | 5/2012 | Lora | F26B 9/003 34/202 |
| 8,517,478 | B2 | 8/2013 | Diemel | |
| 9,013,071 | B1 * | 4/2015 | Levi | A45D 44/02 191/12 R |
| 9,644,834 | B2 * | 5/2017 | Cano | F21V 33/0012 |
| 2003/0042828 | A1 * | 3/2003 | Bonin | A47B 67/02 312/245 |
| 2005/0052100 | A1 * | 3/2005 | Horning | A47B 81/00 312/249.13 |
| 2005/0167563 | A1 * | 8/2005 | Delaney | A45D 20/12 248/475.1 |
| 2005/0264141 | A1 * | 12/2005 | Whitall | A47B 17/04 312/204 |
| 2006/0272170 | A1 * | 12/2006 | Holmes | A47K 10/48 34/275 |
| 2007/0278755 | A1 * | 12/2007 | Jack | A47B 81/00 280/37 |
| 2008/0252189 | A1 * | 10/2008 | Regan | A47B 81/00 312/249.8 |
| 2009/0255891 | A1 | 10/2009 | Lanning | |
| 2010/0224615 | A1 | 9/2010 | Gallo | |
| 2011/0133572 | A1 * | 6/2011 | Levi | A45D 20/14 307/139 |
| 2012/0074121 | A1 | 3/2012 | Gagas | |
| 2014/0210331 | A1 | 7/2014 | Tunzi | |
| 2015/0374121 | A1 * | 12/2015 | Wood | A47B 67/02 312/242 |
| 2016/0211689 | A1 * | 7/2016 | Wang | H02J 7/0045 |
| 2017/0181541 | A1 * | 6/2017 | Stanley, Jr. | H02J 7/025 |
| 2018/0110382 | A1 * | 4/2018 | Jeon | A47K 17/00 |
| 2018/0249826 | A1 * | 9/2018 | Kim | A47B 47/0091 |
| 2018/0249827 | A1 * | 9/2018 | Kim | A47B 47/0091 |
| 2019/0087788 | A1 * | 3/2019 | Murphy | E03D 9/002 |

OTHER PUBLICATIONS

U.S. Office Action dated Nov. 8, 2019 issued in U.S. Appl. No. 15/913,416.

* cited by examiner

BATHROOM MANAGEMENT APPARATUS

CROSS-REFERENCE TO RELATED APPLICATION(S)

This application claims the priority benefit of Korean Patent Application No. 10-2017-0028492, filed in Korea on Mar. 6, 2017 in the Korean Intellectual Property Office, the disclosure of which is incorporated herein by reference.

U.S. application Ser. Nos. 15/913,154; 15/913,257; and 15/913,416, are related and are hereby incorporated by reference in their entirety. Further, one of ordinary skill in the art will recognize that features disclosed in these above-noted applications may be combined in any combination with features disclosed herein.

BACKGROUND

1. Field

A bathroom management apparatus having functional modules that provide storage space and removes humidity is disclosed.

2. Background

Bathroom management apparatus having functional modules are known. However, they suffer from various disadvantages.

BRIEF DESCRIPTION OF THE DRAWINGS

Embodiments will be described in detail with reference to the following drawings in which like reference numerals refer to like elements, and wherein.

DETAILED DESCRIPTION

Figure 1:
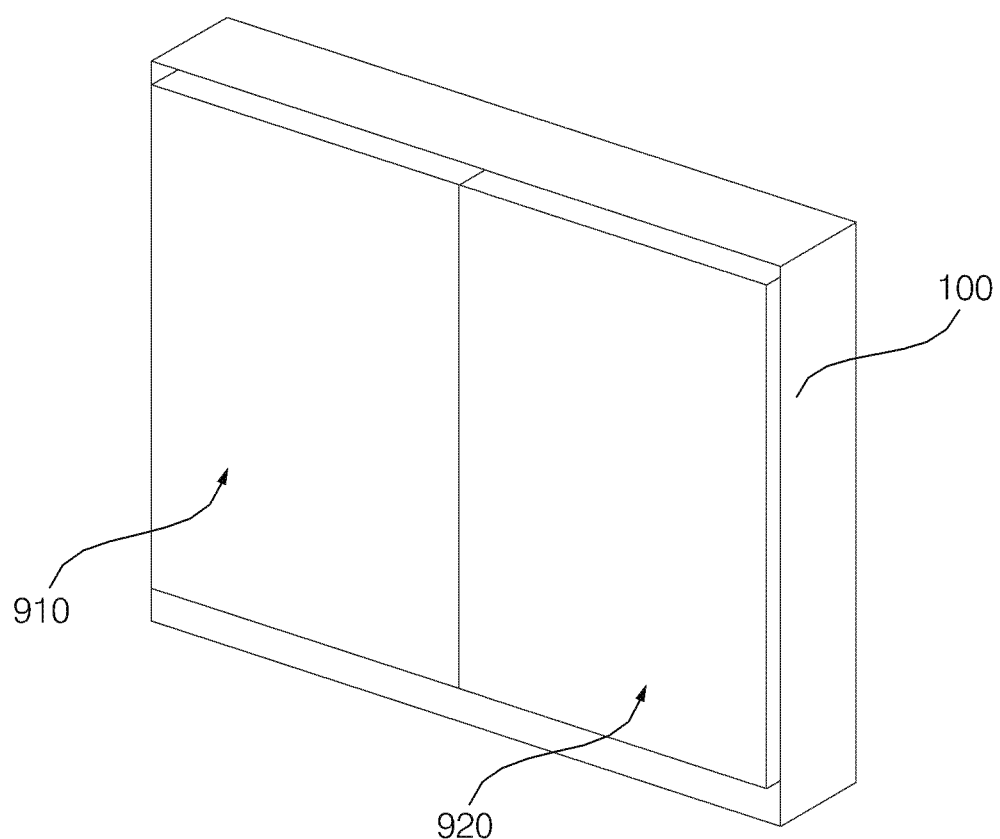
FIG. 1 is a perspective view showing a bathroom management apparatus according to an embodiment of the present disclosure.

Hereinafter, a bathroom management apparatus according to embodiments of the present disclosure will be described in detail with reference to the accompanying drawings.

In general, a bathroom is a place that allows users to wash his/her clothes, face, hands, shower, or the like. Since the bathroom is a very humid place, molds and bacteria may easily breed and may result in unwanted odors.

Most bathrooms dry and deodorize mainly relying on a ventilation fan. However, since an operation of the ventilation fan may not suitable or may be inadequate to dry the whole bathroom even with constant operation, the ventilation fan alone may be inadequate to control mold and the bacteria. Accordingly, it is important to prevent the bathroom from becoming a habitat of the molds and the bacteria by removing moisture early on, particularly at low lying areas of the bathroom, as well as promptly drying wet bath and toilet appliances such as wet towels.

Further, various facilities such as washstand, toilet, mirror, towel rack, toothbrush holder, as well as a storage space (or storage room) for storing various bath and toilet appliances including towels or the like, may be provided in the bathroom. Meanwhile, a user may use various types of electronic products such as hair dryers and shavers in the bathroom.

Hence, if a bathroom management apparatus can integrate multiple functions such as a toothbrush sterilizer, a cosmetics refrigerator, a charging function for electronic products, as well as drying or dehumidifying functions to address multiple needs in the bathroom, the space in the bathroom can be more effectively used.

Further, if a bath management apparatus can be customized to select only desired functions among various function modules including, for example, a storage module having a function for storage, an air conditioning module having a function to dry objects in the bathroom, a sterilizing module having a function of a toothbrush sterilizer, a refrigerating module having a function of a cosmetics refrigerator, and a charging module having a charging function for the electronic products, or the like, the effectiveness and usability of the bathroom management apparatus may be improved.

In addition, an installation position of the function modules may be freely changed by taking into consideration available storage space, convenience and usability to the user. Since a toilet, a washstand, and a mirror may each be installed in different locations in the bathroom, the installation position of the function module may be freely changed according to the applicable environment of the bathroom.

Meanwhile, since a user may desire to quickly dry off after showering in a bathroom, particularly during cold winter months, there is a need for a bathroom management apparatus to selectively allow changes in airflow to dry of the user's body or dry/dehumidify the bathroom by switching flow of air blown from the air conditioning module.

A first objective of the present disclosure provides a bathroom management apparatus capable of selecting dry of the user's body and dry of the bathroom.

A second objective of the present disclosure provides a bathroom management apparatus which allows a user to visually recognize whether the bathroom management apparatus is in a mode for drying a user's body by virtualizing a wind direction or in a mode for drying a bathroom.

The bathroom management apparatus as broadly described and embodied herein addresses these as well as other aspects.

Figure 2:
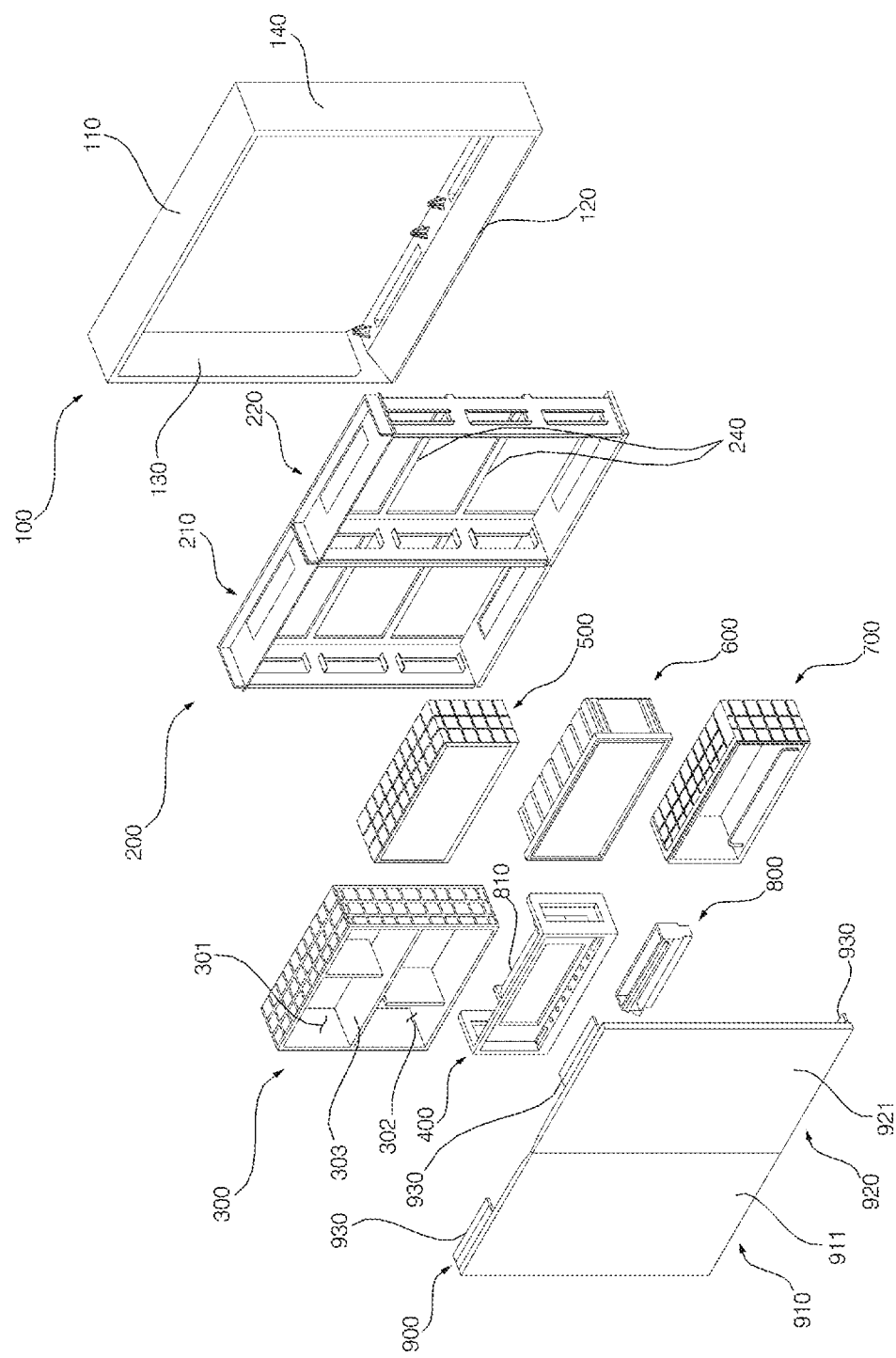
FIG. 2 is an exploded perspective view showing a bathroom management apparatus of FIG. 1.

FIG. 1 is a perspective view showing a bathroom management apparatus according to one embodiment of the present disclosure, and FIG. 2 is an exploded perspective view showing a bathroom management apparatus of FIG. 1. The bathroom management apparatus may include a cabinet 100, a frame 200 installed inside the cabinet 100, a plurality of function modules 300, 400, 500, 600, 700, and 800, and a door 900 disposed in a forward direction of the cabinet 100.

The cabinet 100 may have a hollow structure and may have a square shape of which a front surface and a rear surface are open. The cabinet 100 may form an upper external appearance, a lower external appearance, a left external appearance, and a right external appearance.

The cabinet 100 may include an upper panel 110 forming an upper side, a lower panel 120 forming a lower side, a left side panel 130 forming a left side, and a right side panel 140 forming a right side. The upper panel 110 connects a top end of the left side panel 130 with a top end of the right side panel 140. The lower panel 120 connects a bottom end of the left side panel 130 with a bottom end of the right side panel 140.

A left end of the upper panel 110 may be coupled with a top end of the left side panel 130 and a right end of the upper panel 110 may be coupled with a top end of the right side panel 130. Further, a left end of the lower panel 120 may be coupled with a lower end of the left side panel 130, and a right end of the lower panel 120 may be coupled with a bottom end of the right side panel 140.

The frame 200 may include frame bodies 210 and 220 having a square shape corresponding to the cabinet 100 of which a front surface and a rear surface are open, and back brackets 240 disposed in a rearward direction of the frame bodies 201 and 220 to be coupled with rear surfaces of the frame bodies 210 and 220. The frame bodies 210 and 220 reinforce stiffness of the cabinet 100. The bracket 240 may be thicker than the frame bodies 210 and 220 to reinforce the stiffness of the frame bodies 210 and 220.

The frame bodies 210 and 220 provide a space for multiple function modules 300, 400, 500, 600, 700, and 800. The function modules 300, 400, 500, 600, 700, and 800 include a towel care module 300 (or towel warmer), a sterilizing module 400 (or sterilizer), a secret box module 500 (or lock box), a refrigerating module 600 (or refrigerator), a charging module 700 (or device charger), and a blower out module 800 (or blower module, vane assembly). The towel care module 300, the sterilizing module 400, the secret box module 500, the refrigerating module 600, the charging module 700, and the blower module 800 may be independently provided and installed inside the frame bodies 210 and 220 as module units. Ribs protrude from upward, downward, left and right sides of the function modules 300, 400, 500, 600, 700, and 800, respectively. The ribs protrude from left and right sides of the function modules 300, 400, 500, 600, 700, and 800 may be supported by an inner rib 215 to be described later protruding in the frame bodies 210 and 220.

The towel care module 300 may be installed with a function division plate 303. The function division plate 303 divides an inner space of the towel care module 300. The towel care module 300 may include a first storage space 301 for storing towels at a top side of the function division plate 303 and a second storage space 302 for storing the towels at a bottom side of the function division plate 303, and configured to dry and warm the stored towels. The towel care module 300 may include a first independent towel care module having only the first storage space 301 without the function division plate 303 and a second independent towel care module having only the second storage space 302.

The sterilizing module 400 may be used as a toothbrush sterilizer. The sterilizing module 400 may be installed therein with toothbrushes, and may be installed therein with a lamp for irradiating ultra violet ray to the toothbrushes. A blower module 800 may be installed at a bottom side of the sterilizing module 400. An air conditioning module 810 (or dryer) including a blower for sucking and blowing air to the blower module 800 and a heater for heating the air blown from the blower is installed at a rearward direction of the sterilizing module 400 corresponding to a top side of the blower module 800 so that the sterilizing module 400 and the air conditioning module 810 may be integrally formed. The blower module 800 may exhaust the air blown from the blower into an inside of the bathroom.

The secret box module 500 may be used as storage for storing objects to prohibit children and customers to see or touch. The secret box module 500 may be a lock box, or the like, and may be secured.

The refrigerating module 600 may be used as usage for refrigerating medicines and cosmetics. The refrigerating module 600 may be installed with a thermoelectric module for supplying cold air into the refrigerating module 600 and for emitting warm air to an outside of the refrigerating module 600.

The charging module 700 may be used as usage for charging electronic devices such as a hair dryer and an electric shaver. The charging module 700 may be installed therein with a holder for holding the hair dryer and with a receptacle in which a power plug of the electronic device or a power plug of a charger for charging the electronic device.

Two frame bodies 210 and 220 may be provided and include a first frame body 210 and a second frame body 220 disposed at one side of the first frame body 210. The first frame body 210 and the second frame body 220 have the same structure. The desired modules may be customized based on user need. For example, desired ones among the towel care module 300, the sterilizing module 400, the secret box module 500, the refrigerating module 600, the charging module 700, and the blower module 800 may be selected and installed according to a need of a consumer. For example, only a plurality of towel care modules 300 may be installed, or alternatively, two towel care modules 300 and one refrigerating module 600 may be installed in the frame bodies 210 and 220. According to the number of towel care modules 300, the sterilizing modules 400, the secret box modules 500, the refrigerating modules 600, and the charging modules 700 installed in the frame bodies 210 and 220, one or more frame bodies 210 and 220 may be provided.

The door 900 may form a front external appearance of the bathroom management apparatus. The door 900 opens/closes an open front surface of the cabinet 100. The same number of doors 900 is provided by the corresponding number of the frame bodies 210 and 220. Since the two frame bodies 210 and 220 are provided, two doors 900 are provided to include a first door 910 and a second door 920. The first door 910 may be disposed in a forward direction of the first frame body 210 and opens a left side of an open front surface of the cabinet 100, and the second door 920 may be disposed in a forward direction of the second frame body 220 and opens a right side of an open front surface of the cabinet 100.

Mirrors 911 and 912 may be provided at front surfaces of the first door 910 and the second door 920, respectively. The mirrors 911 and 921 may be used instead of a mirror inside the bathroom. The mirrors 911 and 921 include a first mirror 911 provided at a front surface of the first door 910 and a second mirror 921 provided at a front surface of the second door 920.

A hinge 930 may be installed at a rear surface of the door 900. The hinge 930 may include a first hinge member of which one end is coupled with a rear surface of the door and a second hinge member of which one end is rotatably coupled with an opposite end of the first hinge member and an opposite end is rotatably coupled with the frame bodies 210 and 220. The hinges 930 may be installed at a top side and a lower side of a rear surface of the first door 910, respectively, and may be installed at a top side and a bottom side of a rear side of the second door 910.

Figure 3:
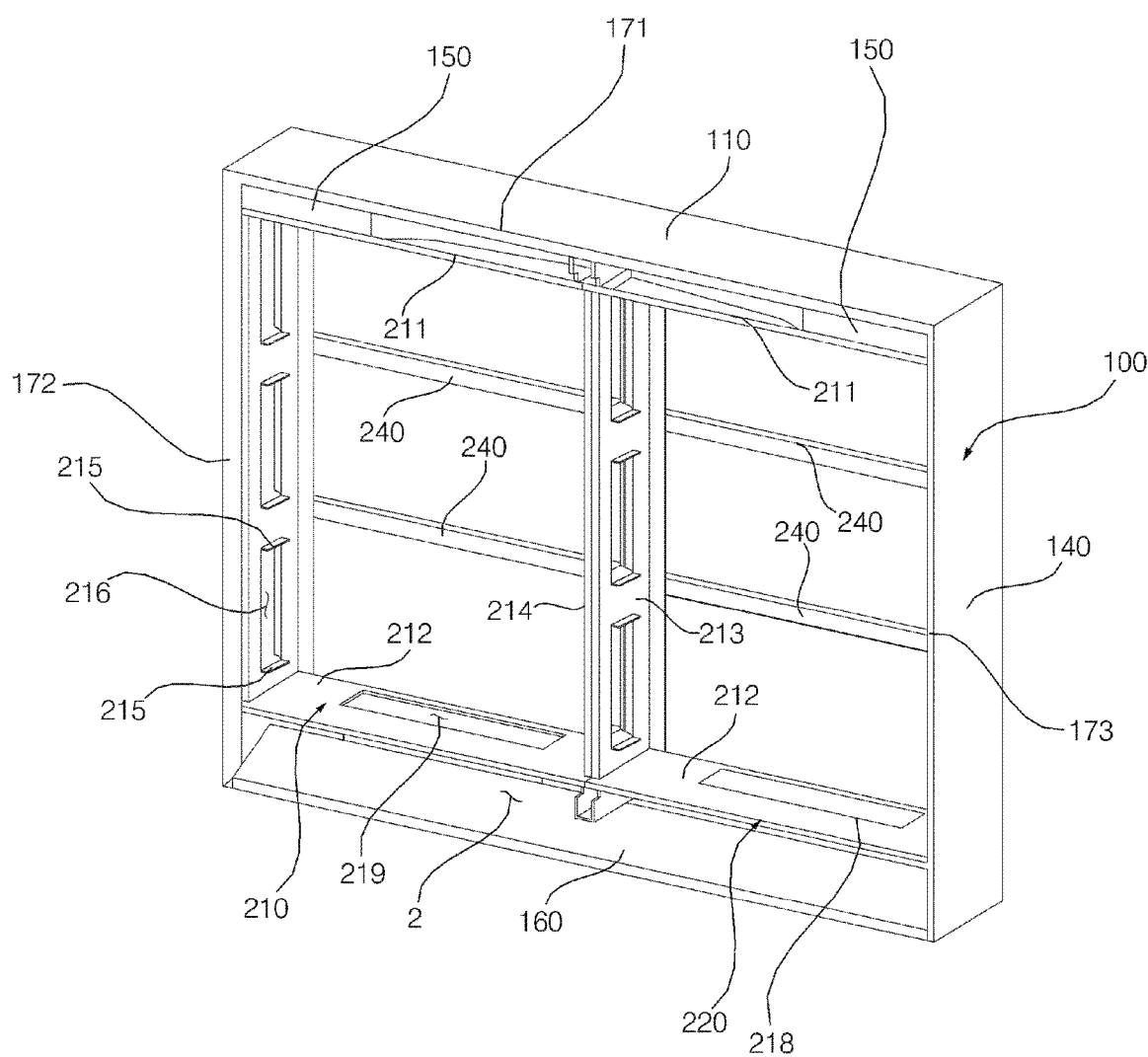
FIG. 3 is a view illustrating a coupled state between the cabinet and the frame.
Figure 4:
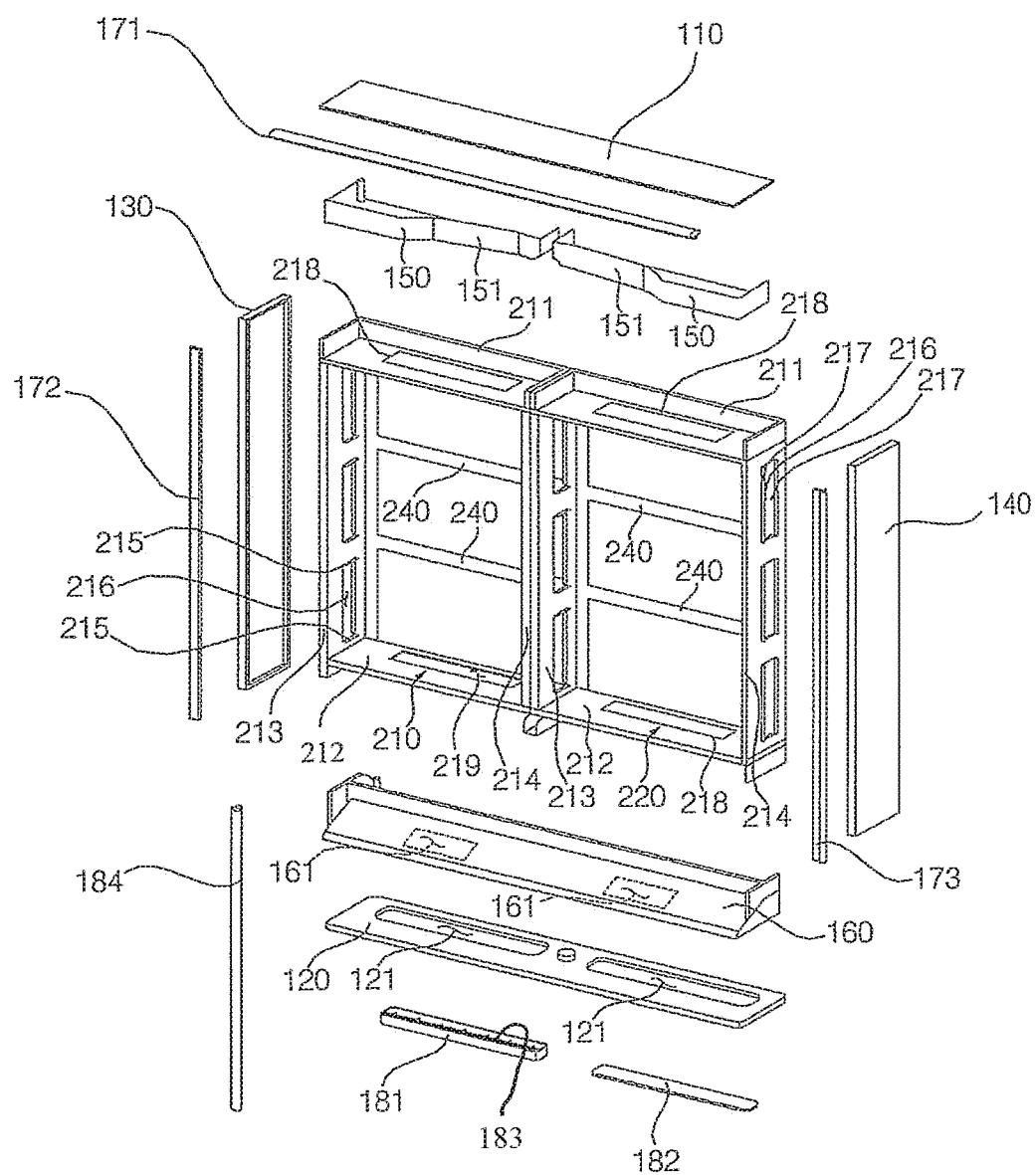
FIG. 4 is an exploded perspective view of FIG. 3.

FIG. 3 is a view illustrating a coupled state between the cabinet and the frame shown in FIG. 3, and FIG. 4 is an exploded perspective view of FIG. 3. Top surfaces and bottom surfaces of frame bodies 210 and 220 may be spaced apart from the cabinet 100. That is, the top surfaces of the frame bodies 210 and 220 may be vertically spaced apart from the upper panel 110 of the cabinet 100, and the bottom surfaces of the frame bodies 210 and 220 may be vertically spaced apart from the lower panel 110 of the cabinet 100.

An upper cover 150 may be disposed at a space between the upper panel 110 of the cabinet 100 and the top surfaces of the frame bodies 210 and 220. The upper cover 150 may be inserted into the space between the upper panel 110 of the cabinet 100 and the top surfaces of the frame bodies 210 and 220 to be coupled with the upper panel 110 of the cabinet 100 and the top surfaces of the frame bodies 210 and 220.

When a door 900 is closed, the upper cover 150 covers the space between the upper panel 110 of the cabinet 100 and the top surfaces of the frame bodies 210 and 220, a hinge 930 installed at a rear top side of the door 900 is not viewable from a rear direction of the bathroom management apparatus through a space between the upper panel 110 and top surfaces of the frame bodies 210 and 220. When the door 900 is open, the upper cover 150 prevents the bathroom wall from being viewed from the forward direction of the bathroom management apparatus through a space between the upper panel 110 and the top surface of the frame bodies 210 and 220. The upper cover 150 may have a shape in which a top surface and a rear surface are open to include a bottom surface, a front surface, a left surface, and a right surface.

A concave groove 151 for receiving a hinge 930 when the door 900 is closed is formed at the front surface of the upper cover 150 so that a space for receiving the hinge 930 may be formed between the upper panel 110 and the top surfaces of the frame bodies 210 and 220.

Further, a control panel 160 may be inserted between the lower panel 120 of the cabinet 100 and bottom surfaces of the frame bodies 210 and 220. The control panel 160 may be inserted between the lower panel 120 of the cabinet 100 and bottom surfaces of the frame bodies 210 and 220 to be coupled with the lower panel 120 of the cabinet 100 and the bottom surfaces of the frame bodies 210 and 220.

Remaining regions of the control panel 160 except for a top side coupled with the bottom surfaces of the frame bodies 210 and 220 may be spaced apart from the bottom surfaces of the frame bodies 210 and 220. Air exhausted from the blower module 800 may be moved into a first air outlet 2 through a space between bottom surfaces of the frame bodies 210 and 220 and a top side of the control panel 160. Hence, after a shower, the user may dry off using air exhausted through the first air outlet 2.

A user interface as well as an input unit for controlling function modules 300, 400, 500, 600, 700, 800, and 810 may be installed at the control panel 160. The input unit may include at least one of a button and a touch screen, and the user pushes or touches the input unit to operate or stop the function modules 300, 400, 500, 600, 700, 800, and 810. An installed region of the input unit of the control panel 160 may be exposed below the door 900 when the door 900 is closed.

Meanwhile, the cabinet 100 may include decoration members 171, 172, and 173 coupled with a front end of the upper panel 110, a front end of the left side panel 130, and a front end of the right side panel 140, respectively. The decoration members 171, 172, and 173 include a first decoration member 171 coupled with a front end of the upper panel 100, a second decoration member 172 coupled with a front end of the left side panel 130, and a third decoration member 173 coupled with a front end of the right side panel 140. The decoration members 171, 172, and 173 are not installed at a front end of the lower panel 120. Instead, the front end of the lower panel 120 may be covered by a front end of the control panel 160. That is, the control panel 160 may function as a decoration members by covering the front end of the lower panel 120. The control panel 160 may be formed with the same color and material as those of the decoration members 171, 172, and 173. The frame bodies 210 and 220 may include an upper frame 211 forming an upper side, a lower frame 212 forming a lower side, and a left side frame 213 forming a left side, and a right side frame 214 forming a right side.

The upper frame 211 connects a top end of the left side frame 213 with a top end of the right side frame 214. The lower frame 212 connects a bottom end of the left side frame 213 with a bottom end of the right side frame 214.

A left end of the upper frame 211 may be coupled with a top end of the left side frame 213, and a right end of the upper frame 211 may be coupled with a top end of the right side frame 214. Further, a left end of the lower frame 212 may be coupled with a bottom end of the left side frame 213, and a right end of the lower frame 212 may be coupled with a bottom end of the right side frame 214.

The upper frame 211 and the lower frame 212 may have the same structure. The left side frame 213 and the right side frame 214 may have the same structure. Accordingly, the frame body 210 and the second frame body 220 may be installed inside the cabinet 100 regardless of upper and lower sides and regardless of left and right sides.

The upper frame 211 may have a shape in which a top surface and a front surface are open and may include a bottom surface, a left surface, a right surface, and a rear surface. Further, the lower frame 212 has a shape that is upside down relative to the upper frame 211 and may include a bottom surface and a front surface which are open. That is, the lower frame 212 may include a left surface, a right surface, and a rear surface.

First opening portions 216 having a square shape may be formed in the left side frame 213 and the right side frame 214, respectively. The first opening portion 216 may form a path through which wires of the function modules 300, 400, 500, 600, 700, and 800 may pass. A same number of first opening portions 216 may be formed corresponding to the number of function modules 300, 400, 500, 600, 700, and 800 installed inside the frame bodies 210 and 220.

Inner ribs 215 may be formed at inner sides of the left side frame 213 and the right side frame 214, respectively. The inner ribs 215 protrudes inward from the frame bodies 210 and 220 at a top side and a bottom side of the first opening portion 216.

The inner rib 215 may guide insertion of the function modules 300, 400, 500, 600, 700, and 800 when the function modules 300, 400, 500, 600, 700, and 800 are individually inserted into the frame bodies 210 and 220. After the function modules 300, 400, 500, 600, 700, and 800 are inserted into the frame bodies 210 and 220, the inner rib 215 may support the function modules 300, 400, 500, 600, 700, and 800.

Outer ribs 217 may be formed at outer sides of the left side frame 213 and the right side frame 214, respectively. The outer ribs 217 may protrude to outer sides of the frame bodies 210 and 220 from a front side and a rear side of the first opening portion 216, respectively.

The outer ribs 217 may be spaced a part from each other in forward and reward directions while interposing the first opening portion 216 therebetween to form a path through which wires of the function modules 300, 400, 500, 600, 700, and 800 pass after the wires of the function modules 300, 400, 500, 600, 700, and 800 pass through the first opening portion 216.

Cut lines 218 having a square shape are formed at a bottom surface of the upper frame 211 and a top surface of the lower frame 212, respectively. The cut lines 218 may be formed by partially cutting a bottom surface of the upper frame 211 and a top surface of the lower frame 212 so that a worker may easily separate an inner region divided by the cut lines 218 from a bottom surface of the upper frame 211 an a top surface of the lower frame 212.

When the sterilizing module 400 is installed close to the upper frame, a worker may cut the cut line 218 formed at the upper frame 211 among the cut line 218 formed at the upper frame 211 and the cut line 218 formed at the lower frame 212 to separate an inner region of the upper frame 211 divided by the cut line 218. When the sterilizing module 400 is installed close to the lower frame, the worker may cut the cut line 218 formed at the lower frame 211 among the cut line 218 formed at the upper frame 211 and the cut line 218 formed at the lower frame 212 to separate an inner region of the lower frame 212 divided by the cut line 218.

The second opening portions 219 may be formed at the upper frame 211 and the lower frame 212 when the inner region divided by the cut line 218 is separated by the worker. Further, a third opening portion 161 may be formed at a lower side of the second opening portion 219 in a lower side of the control panel 160. Further, a fourth opening portion 121 may be formed at a lower side of the third opening portion 161 in a lower panel 120 of the cabinet 100.

A blower louver 181 or a lower cover 182 may be provided at the fourth opening portion 121. The blower louver 181 may be installed at a region corresponding to the fourth opening portion 121 or a lower cover 182 may be installed on the top surface of the lower panel 120. When the fourth opening portion 121 is located under the sterilizing module 400, for example, the blower louver 181 may be installed at a region corresponding to the fourth opening portion 121 in the lower panel 120. Otherwise, a lower cover 182 may be installed at a region corresponding to the fourth opening portion 121 in the lower panel 120 so that the fourth opening portion 121 is shielded by the lower cover 182.

The blower louver 181 may include a discharge grill 183, and may be installed at a region corresponding to the fourth opening portion 121 in the lower panel 120 to guide air from the blower module 800 into the fourth opening portion 121. When the blower louver 182 is installed at a region corresponding to the fourth opening portion 121 in the lower panel 120, the fourth opening portion 121 becomes the second air outlet 121. That is, in the cabinet 100, the first air outlet 2 is spaced apart from a lower frame 212 being a bottom surface of the frame 200, and a second air outlet 121 may be formed at a bottom surface of the frame 200.

The blower module 800 may be disposed inside the control panel 160 between the lower panel 120 and the lower frame 212. Further, a top end of the blower module 800 may be inserted into the second opening portion 219 so that air blown from the blower flows though the blower module 800, and a bottom end of the blower module 800 is connected to the blower louver 181 through the third opening portion 161. Moreover, a front opening portion communicating with the first air outlet 2 may be formed at a front surface of the blower module 800.

Since the blower module 800 may be installed with a motor and a fluid path switching vane rotated by a driving force of the motor, the fluid path switching vane is rotated by the driving force of the motor to open the front opening portion and close a bottom end, such that air flowing from an air conditioning module 810 passes through the front opening portion and is discharged into the bathroom through the first air outlet 2. When the front opening portion is closed and the bottom end is open, the air flowing from the blower passes through the blower louver 181 and is discharged into the bathroom through the second air outlet 121. That is, the blower module 800 switches the direction of air blown from the air conditioning module 810 to one of the first air outlet 2 and the second air outlet 121.

A user may control a rotation position of the fluid path switching vane of the blower module 800 by operating the input unit installed at the control panel 160 to discharge air into the bathroom through the first air outlet 2 or to discharge the air into the bathroom through the second air outlet 121. The air discharged into the bathroom through the first air outlet 2 may be used to dry the user's body. The air discharged into the bathroom through the second air outlet 121 may be used to dry an inside of the bathroom.

Meanwhile, when a plurality of frame bodies 210 and 220 are provided, a center cover 184 may be further installed at front surfaces of adjacent side frames 214 and 213 of the plurality of frame bodies 210 and 220. That is, in the present embodiment, two frame bodies 210 and 220 are provided, center covers 184 may be installed at a front surface of the right side frame 214 of the first frame body 210 and a front surface of a left side frame 213 of the second frame body 220, respectively. The center cover 184 may cover the right side frame 214 of the first frame body 210 and the left side frame 213 of the second frame body 220 in a forward direction. In addition, after the function modules 300, 400, 500, 600, and 700 are inserted into the frame bodies 210 and 220, the center cover 184 may protrude to both sides of the function modules 300, 400, 500, 600, and 700 to cover a module locking rib which is locked at a front surface of the both side frames 213 and 214 of the frame bodies 210 and 220.

Figure 5:
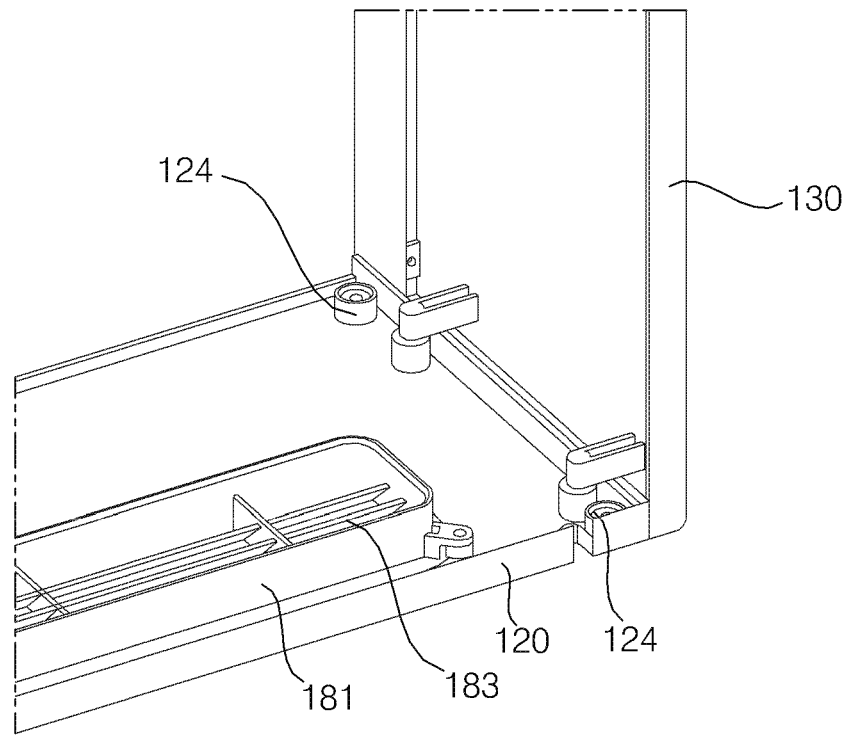
FIG. 5 is a rear perspective view illustrating a lower panel and a left side panel shown in FIG. 4.
Figure 6:
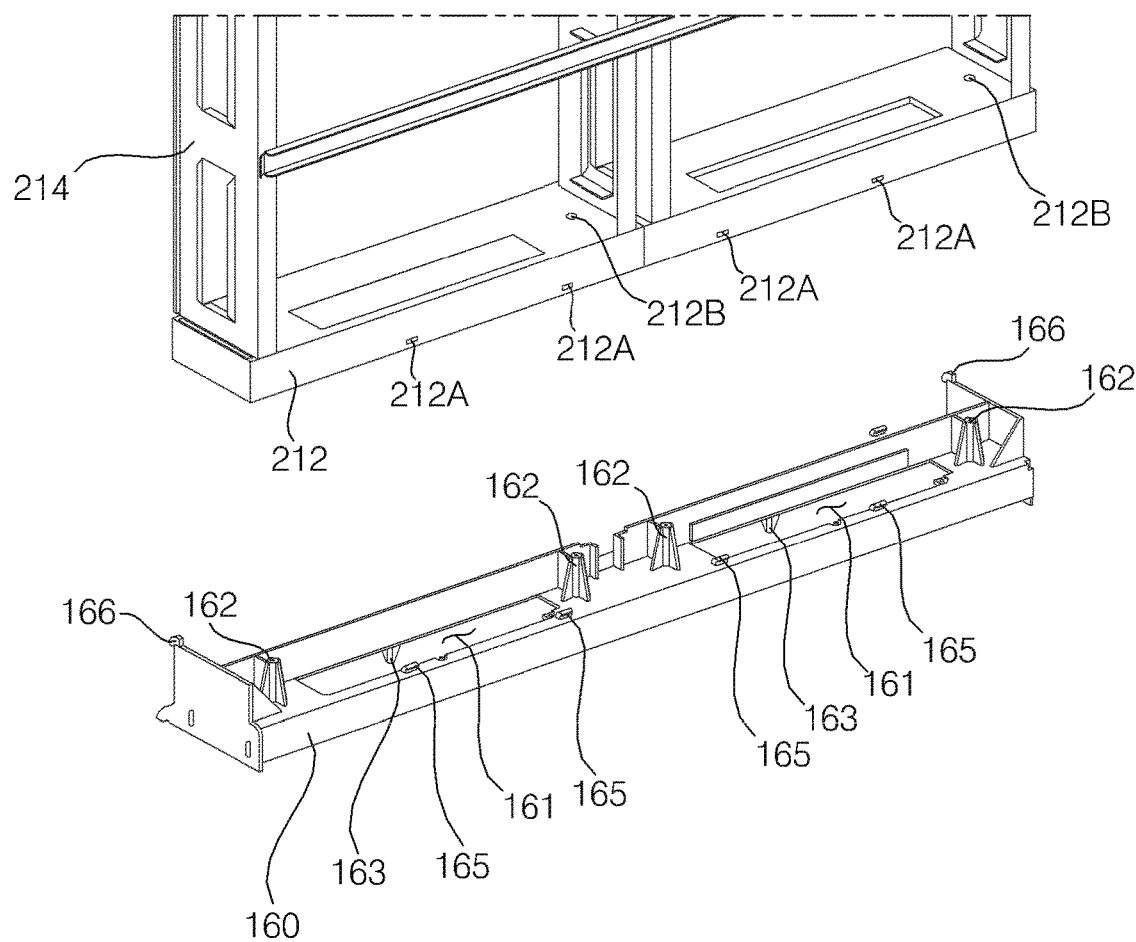
FIG. 6 is an exploded perspective view illustrating a lower frame and a control panel.
Figure 7:
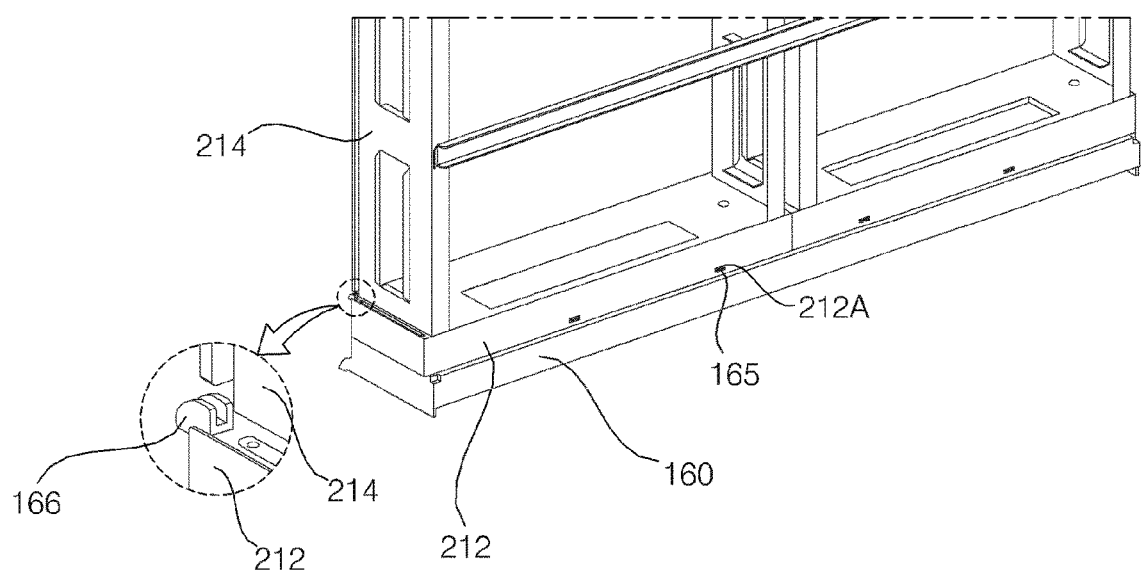
FIG. 7 is a combined perspective view illustrating a lower frame and a control panel shown in FIG. 4.

FIG. 5 is a rear perspective view illustrating a lower panel and a left side panel shown in FIG. 4, FIG. 6 is an exploded perspective view illustrating a lower frame and a control panel, and FIG. 7 is a combined perspective view illustrating a lower frame and a control panel shown in FIG. 4

A hook hole 212A may be formed at a rear surface of the lower frame 212. A plurality of hook holes 212A is spaced apart from each other right to left. Two holes 212A may be formed in one of frame bodies 210 and 220.

Further, the control panel 160 may be formed therein with a first hook protrusion 165 inserted and locked in the hook hole 212A and a second hook protrusion 166 locked with a top end of the lower frame 212. The same number of first hook protrusions 165 may be formed at a position corresponding to the hook holes 212A by the corresponding number of the hook holes 212A. The first hook protrusion 165 protrudes rearward from an upper rear portion of the control panel 160. The second hook protrusion 166 protrudes rearward from both front portions of the control panel 160. The control panel 160 is moved from a forward direction of the lower frame 212 to a rearward direction thereof to insert the first hook protrusion 165 into the hook hole 212A. Next, the control panel 160 is optionally locked with a lower frame 212 of the frame 200 by locking the second hook protrusion 166 with a top end of the lower frame 212.

The control panel 160 may further include a second locking boss 162 locked with a lower frame 212 of the frame 200 and a third locking boss 163 locked with a lower panel of a cabinet 100. The second locking boss 162 protrudes upward from a top surface of the control panel 160 and the third locking boss 163 protrudes downward from a bottom surface of the control panel 160.

A plurality of second locking bosses 162 may be spaced apart from each other rightward and leftward. In the present embodiment, two second locking bosses 162 are formed in one of frame bodies 210 and 220. Further, the lower frame 212 is formed therein with a locking hole 212B locked with the locking boss 162 through a screw. It is preferred that the same number of locking holes 212B may be formed at a position corresponding to the second boss 162 by the corresponding number of the second boss 162.

After the control panel 160 is optionally locked with the lower frame 212 using the first hook protrusion 165 and the second hook protrusion 166, the screw may be inserted into the locking hole 212B from a top side of the lower frame 212 to be locked with the second locking boss 162 so that the control panel 160 is locked with a lower frame 212 of the frame 200. Moreover, a screw is inserted from a bottom side of the lower panel 120 of the cabinet 100 to lock a locking rib 124 formed at a top surface of the lower panel 120 with a third locking boss 163 formed at a bottom surface of the control panel 160 so that the control panel 160 is locked with a lower panel 120 of the cabinet 100.

Figure 8:
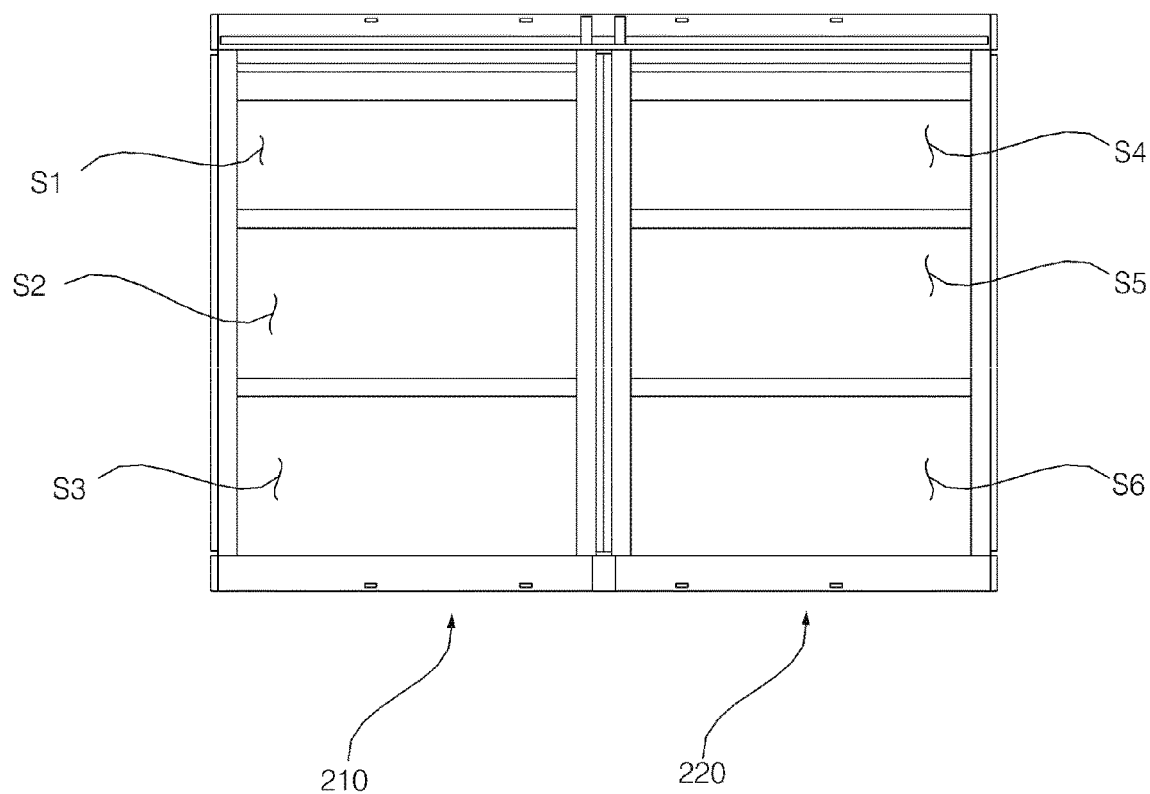
FIG. 8 is a front view illustrating a frame of a bathroom management apparatus according to an embodiment of the present disclosure.

FIG. 8 is a front view illustrating a frame of a bathroom management apparatus according to an embodiment of the present disclosure. Referring to FIG. 2 and FIG. 8, frame bodies 210 and 220 may include mounting spaces S1, S2, S3, S4, S5, and S6 in which function modules 300, 400, 500, 600, and 700 may be inserted and mounted. The mounting spaces S1, S2, S3, S4, S5, and S6 may include a first mounting space S1 located at the upper most side inside the first frame body 210, a second mounting space S2 located at a center of the first frame body 210, a third mounting space S3 located at the lower most side of the first frame body 210, a fourth mounting space S4 located at the upper most side inside the second frame body 220, a fifth mounting space S5 located at a center of the second frame body 220, and a sixth mounting space S6 located at the lower most side of the second frame body 210.

The first mounting space S1, the second mounting space S2, the third mounting space S3, the fourth mounting space S4, the fifth mounting space S5, and the sixth mounting space S6 may have the same size.

The second mounting space S2 is located at a bottom side of the first mounting space S1. The third mounting space S3 is located at a bottom side of the second mounting space S2. The fifth mounting space S5 is located at a bottom side of the fourth mounting space S4. The sixth mounting space S6 is located at a bottom side of the fifth mounting space S5.

The fourth mounting space S4 is located at one side of the first mounting space S1. The fifth mounting space S5 is located at one side of the second mounting space S2. The sixth mounting space S6 is located at one side of the third mounting space S3.

The first mounting space S1 and the fourth mounting space S4 may be located at the same height. The second mounting space S2 and the fifth mounting space S5 may be located at the same height. The third mounting space S3 and the sixth mounting space S6 may be located at the same height. The first mounting space S1, the second mounting space S2, the third mounting space S3, the fourth mounting space S4, the fifth mounting space S5, and the sixth mounting space S6 may have the same vertical length and the same horizontal length.

The towel care module 300 may be inserted and mounted in the first mounting space S1 and the second mounting space S2, or alternatively, the second mounting space S2 and the third mounting space S3, which are adjacent mounting spaces among the first mounting space S1, the second mounting space S2, and the third mounting space S3. Further, the towel care module 300 may be inserted and mounted in the fourth mounting space S4 and the fifth mounting space S5, or alternatively, the fifth mounting space S5 and the sixth mounting space S6, which are adjacent mounting spaces among the fourth mounting space S4, the fifth mounting space S5, and the sixth mounting space S6.

The sterilizing module 400, the secret box module 500, the refrigerating module 600, and the charging module 700 may be mounted in one of the first mounting space S1, the second mounting space S2, the third mounting space S3, the fourth mounting space S4, the fifth mounting space S5, and the sixth mounting space S6.

In the present embodiment, the towel care module 300 is inserted and mounted in the first mounting space S1 and the second mounting space S2. The sterilizing module 400 is inserted and mounted in the third mounting space S3. The secret box module 500 is inserted and mounted in the fourth mounting space S4. The refrigerating module 600 is inserted and mounted in the fifth mounting space S5. The charging module 700 is inserted and mounted in the sixth mounting space S6.

Since the towel care module 300 is formed by integrating the first towel care module and the second towel care module as one, the towel care module 300 has double the length of the sterilizing module 400, the secret box module 500, the refrigerating module 600, and the charging module 700, and hence, the towel care module 300 is inserted and mounted in the first mounting space S1 and the second mounting space S2. When the first towel care module and the second towel care module are separately provided, the first towel care module is inserted and mounted in one of the first mounting space S1 and the second mounting space S2, and the second towel care module may be is inserted and mounted in the other.

The towel care module 300 has double the length of that of the sterilizing module 400, the secret box module 500, the refrigerating module 600, and the charging module 700, which may have the same horizontal length.

Figure 9:
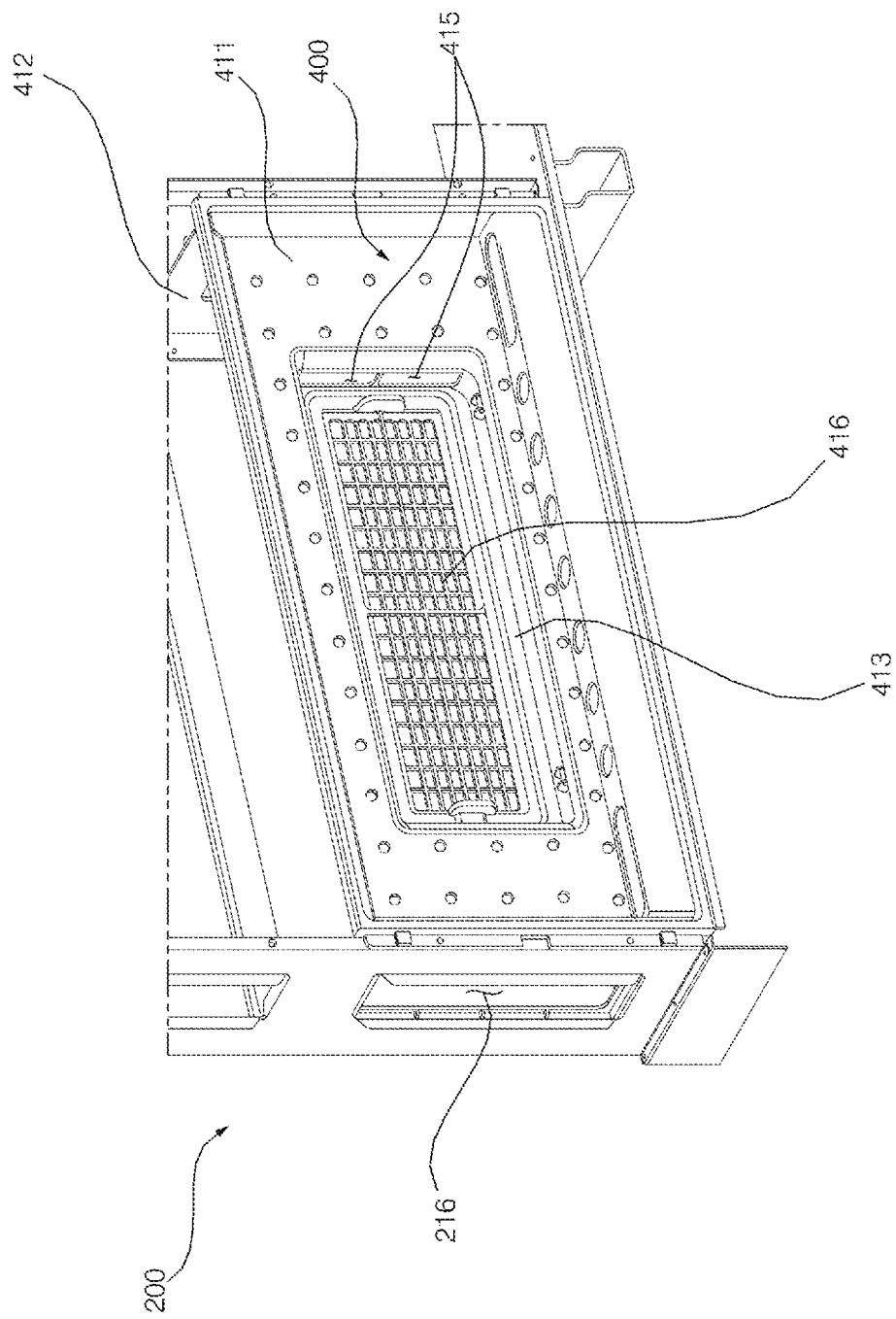
FIG. 9 is a front perspective view illustrating a state of a sterilizing module shown in FIG. 2 mounted on a frame.
Figure 10:
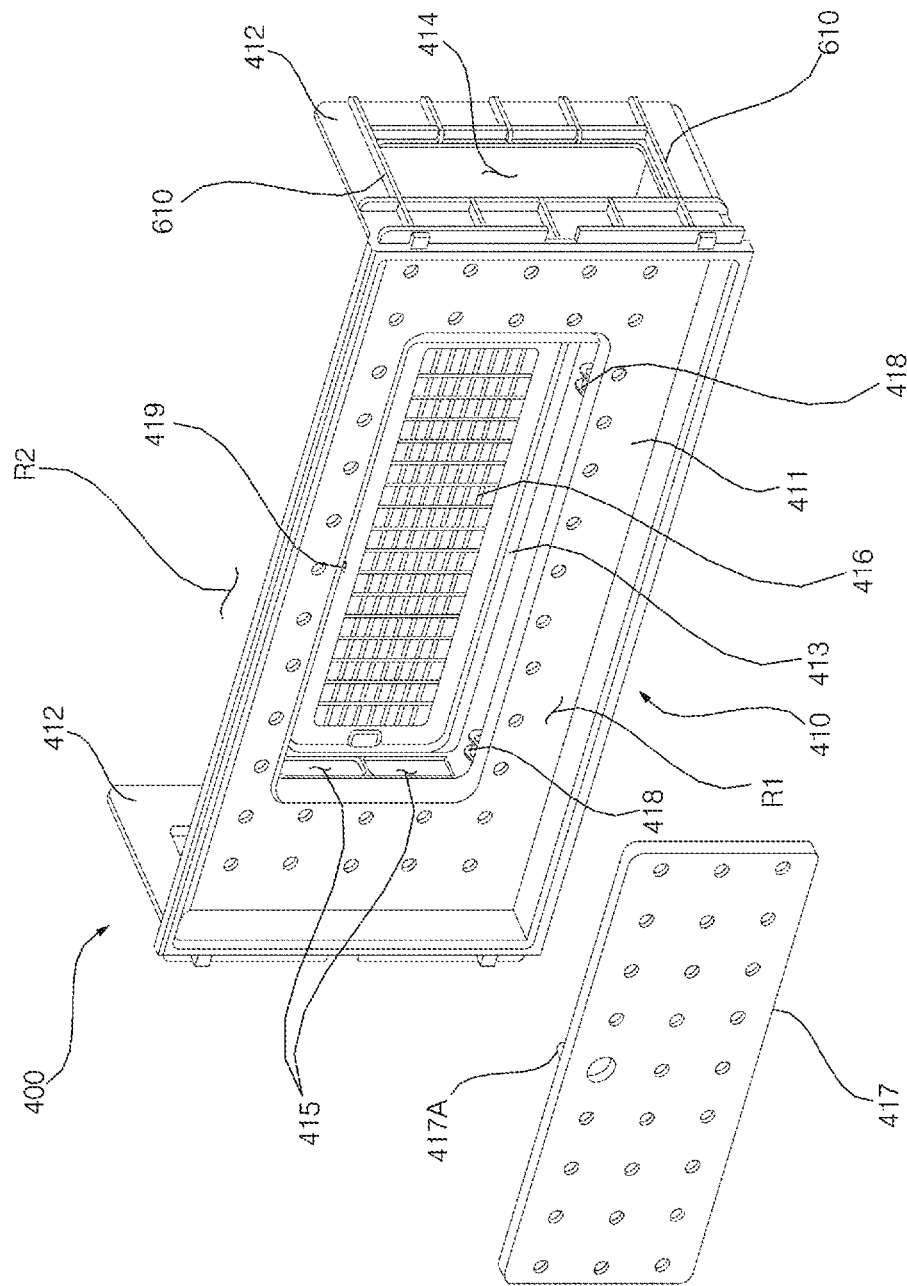
FIG. 10 is a view illustrating an outer case of a sterilizing module and an inner door shown in FIG. 9.
Figure 11:
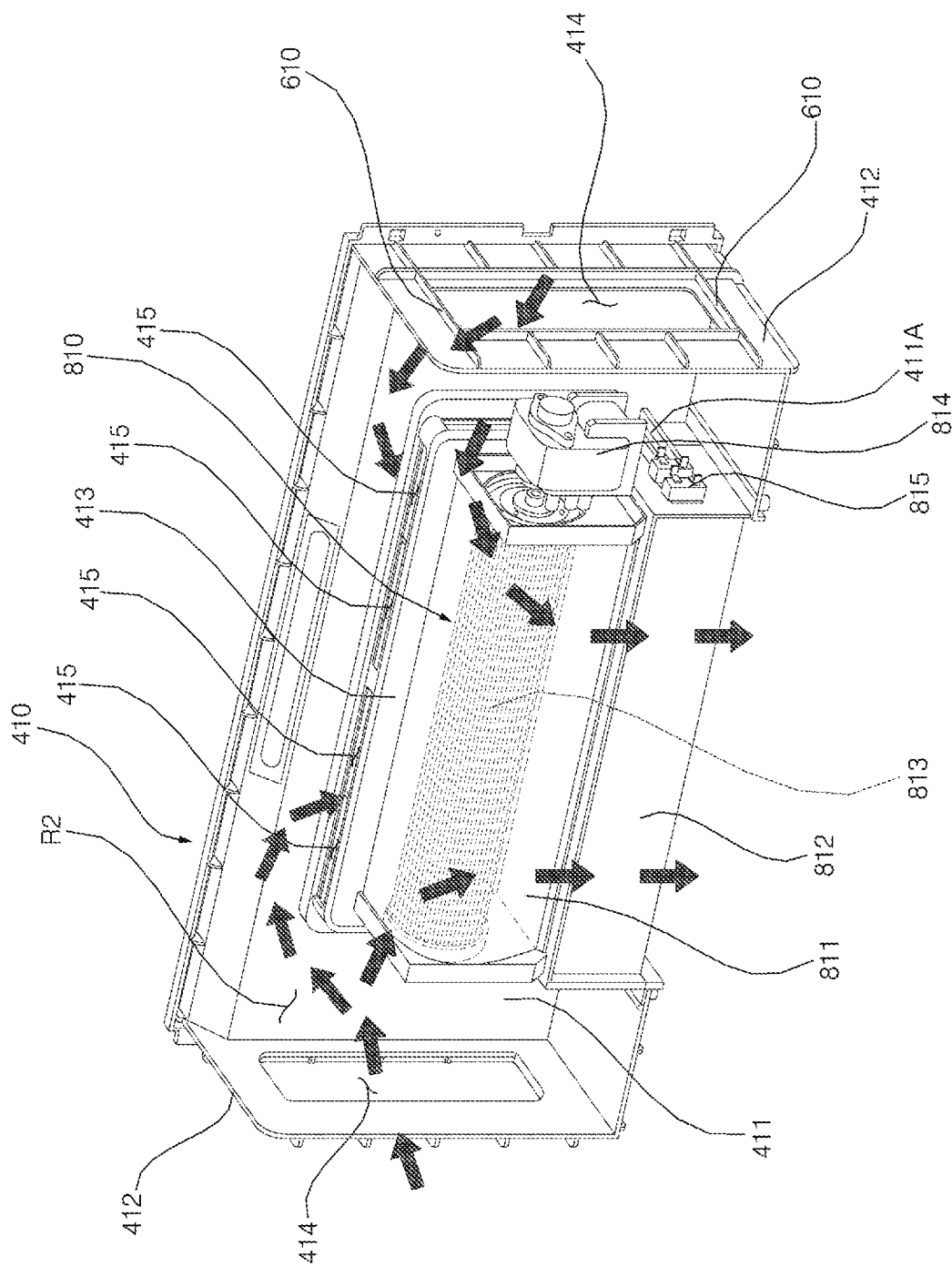
FIG. 11 is a rear perspective view illustrating the sterilizing module shown in FIG. 2.
Figure 12:
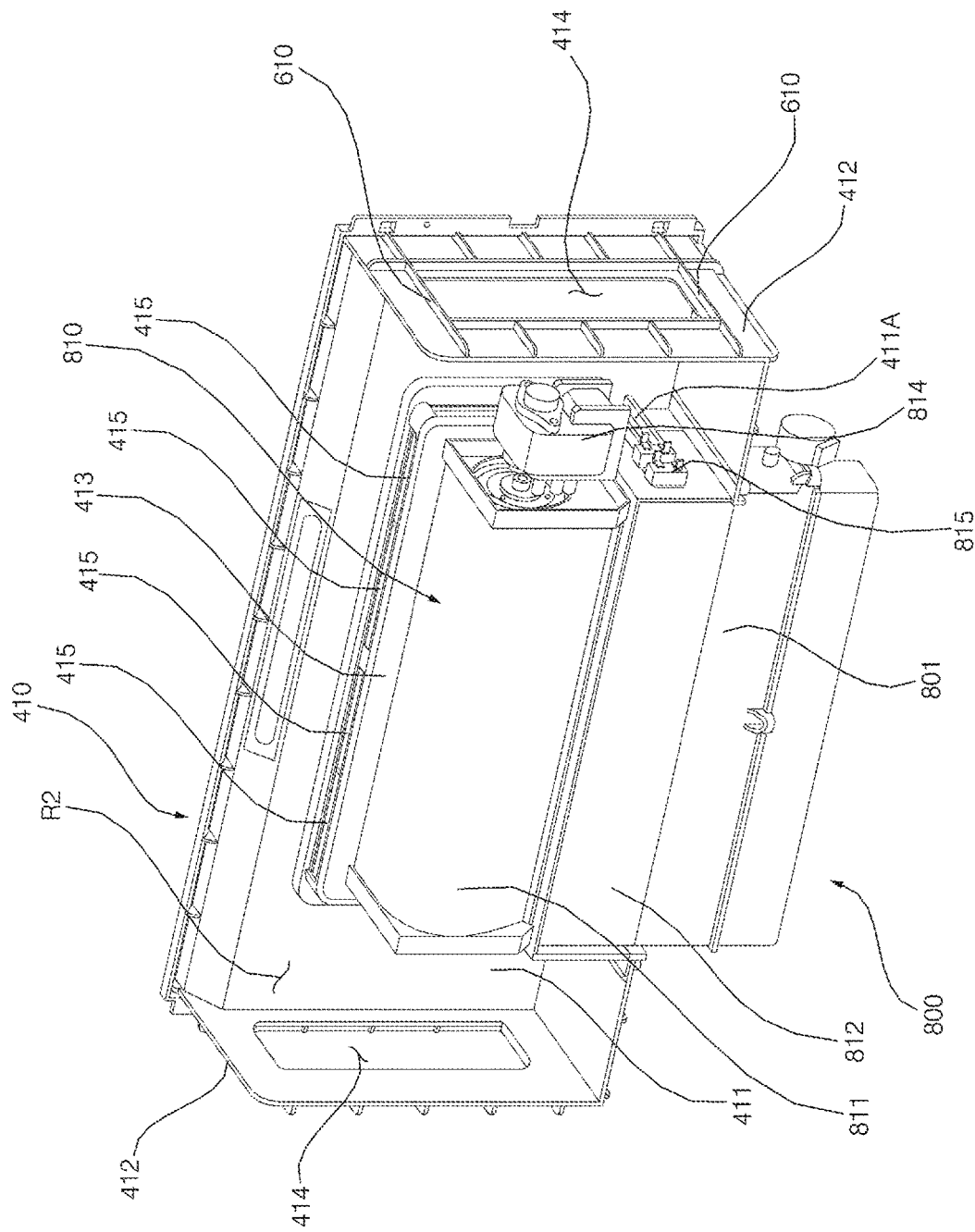
FIG. 12 is a view illustrating a state of the blower out module connected with an air conditioning module shown in FIG. 11.

FIG. 9 is a front perspective view illustrating a state of a sterilizing module shown in FIG. 2 mounted on a frame, FIG. 10 is a view illustrating an outer case of a sterilizing module and an inner door shown in FIG. 9, FIG. 11 is a rear perspective view illustrating the sterilizing module shown in FIG. 2, and FIG. 12 is a view illustrating a state of the blower out module connected with an air conditioning module shown in FIG. 11.

Referring to FIG. 9 to FIG. 12, the air conditioning module 810 is mounted in a rearward direction of the sterilizing module 400. However, in the present embodiment, although the air conditioning module 810 is mounted in the sterilizing module 400, since the air conditioning module 810 sucks and blows air inside the cabinet 100 to the blower out module 800, the air conditioning module 810 may be mounted the closest to the blower out module 800 inside the frame among the towel care module 300, the sterilizing module 400, the secret box module 500, the refrigerating module 600, and the charging module 700. That is, as shown in FIG. 8, when the frame bodies 210 and 220 is provided as one first frame body 910, the air conditioning module 810 may be mounted in the third mounting space S3 among the function modules 300, 400, 500, 600, and 700. The frame bodies 210 and 220 include two bodies of the first frame body 210 and the second frame body 220, the air conditioning module 810 may be mounted in the third mounting space S3 or the sixth mounting space S6 among the function modules 300, 400, 500, 600, and 700. It is preferred that an outer case of the air conditioning module 810 among the function modules 300, 400, 500, 600, and 700 has the same structure as that of the outer case 410 of the sterilizing module 400 to be described later. Hereinafter, the following is that the air conditioning module 810 is mounted in the sterilizing module 400 mounted in the third mounting space S3.

An outer case 410 of the sterilizing module 400 may include a front surface 411 and lateral surfaces 412 protruding rearward from both sides of the front surface 411, respectively. The front surface 411 may be divided into a storage space R1 of a unique function of the sterilizing module 400 and a storage space R1 of the air conditioning module. That is, an outer case 410 of the sterilizing module 400 is open and is formed therein with a storage space R1 of a sterilizing function for storing productions (here, toothbrush) to be sterilized forward based on the front surface 411 and a storage space R2 of a sterilizing function rearward based on the front surface 411.

A front side 411 may be formed therein with an air conditioning module coupling part 413 (or dryer module coupling part, recess) having a shape of which the front surface 411 is recessed and a rear side protrudes rearward. The air conditioning module 810 may be mounted in the air conditioning module coupling part 413 at a rear surface of the air conditioning module coupling part 413. Air conditioning module cases 811 and 812 among components of the air conditioning module 810 are coupled with the air conditioning module coupling part 413. Front surfaces of the air conditioning module cases 811 and 812 coupled with the air conditioning module coupling part 413 is open and a region of the air conditioning module coupling part 413 coupled with the front surfaces of the air conditioning module cases 811 and 812 is open so that the air conditioning module coupling part 413 communicates with insides of the air conditioning module cases 811 and 812.

A guide rib 610 is formed at an outer side of the lateral surface 412. The guide rib 610 is supported by inner ribs 215 formed at both side frames 213 and 214 of the frame 200, respectively. Moreover, a first air inlet 414 is formed at the lateral surface 412. The first air inlet 414 has the same square shape as that of the first opening portions 216 formed at the both side frames 213 and 214 of the frame 200 to communicate with the first opening portions 216, respectively. Accordingly, air inside the cabinet 100 may sequentially pass through the first opening portion 216 and the first air inlet 414 to be sucked into an inner side of the lateral surface 412.

Furthermore, the air conditioning module coupling part 413 is formed therein with a second air inlet 415 for sucking air which is sucked into an inner side of the lateral surface 412 through the first air inlet 414. The second air inlets 415 are formed at a top surface and both surfaces of the air conditioning module coupling part 413, respectively. Since the sterilizing module 400 is mounted in the third mounting space S3 disposed at the lower most side among the first mounting space S1, the second mounting space S2, and the third mounting space S3, the second air inlets 415 may be formed at the top surface of the air conditioning module coupling part 413 as well as both surfaces of the air conditioning module coupling part 413 to uniformly suck air inside the cabinet 100.

Furthermore, in the air conditioning module coupling part 413, a suction grill 416 is disposed rearward of the second air inlet 415 and an inner door 417 is disposed forward of the second air inlet 415. The suction grill 416 is disposed at a region of the air conditioning module coupling part 413 communicating with the air conditioning module cases 811 and 812 to prevent foreign materials from being introduced in the air conditioning module cases 811 and 812. An antibacterial filter may be provided rearward of the suction grill 416.

In addition, since the inner door 417 is installed to open/close an open front side of the air conditioning module coupling part 413, the inner door 417 normally shields the open front side of the air conditioning module coupling part 413. When the user cleans the suction grill 416, the inner door 417 may be open by the user. The inner door 417 is rotatably coupled with a hinge axis 418 of which a bottom end is provided a lower side of the open front side of the air conditioning module coupling part 413. A locking protrusion 417A is formed at a rear top end of the inner door 417 which is inserted and locked in a protrusion 419 provided at a top surface of the open front side of the air conditioning module coupling part 413. If the user pushes a top side of the inner door 417 once while closing the inner door 417, protrusion of the locking protrusion 417A in the protrusion 419 is released so that the inner door 417 may be rotated based on the hinge axis 418 to be open. If the user pushes the top side of the inner door 417 while closing the inner door 417 in a state that the inner door 417 is open, the locking protrusion 417A is locked in the protrusion 419.

The air conditioning module 810 (or dryer) is coupled with the air conditioning module coupling part 413, and includes air conditioning module cases 811 and 812 communicating with the second air inlet 415, a blowing fan 813 rotatably disposed inside the air conditioning module cases 811 and 812, a fan motor 814 configured to rotate the blowing fan 813, and a heater 815 disposed inside the air conditioning module cases 811 and 812 to heat air blown from the blowing fan 813.

Front surfaces of the air conditioning module cases 811 and 812 coupled with the air conditioning module coupling part 413 is open, and bottom ends of air conditioning module cases 811 and 812 connected with a top end of the blower out module 800 is open.

Front surfaces and bottom ends of the air conditioning module cases 811 and 812 are open. The air conditioning module cases 811 and 812 may include an upper air conditioning module case 811 in which the blowing fan 813 and the fan motor 814 and a lower air conditioning module case 811 of which a top end and a bottom end are open and in which a heater 815 is installed. In this case, an open front surface of the upper air conditioning module case is coupled with the air conditioning module coupling part 413. An open top end of the air conditioning module case 812 is connected to an open bottom end of the upper air conditioning module case 811. An open bottom end of the air conditioning module case 812 is connected to a blower out module case 801 (or vane assembly case) of the blower out module 800. Hereinafter, the air conditioning module cases 811, 812 (or dryer case) formed by integrating the lower air conditioning module case 812 with the upper air conditioning module case 811 will be described.

The blowing fan 813 includes a cross flow fan which may be formed to be axially long. One end of a rotation axis of the blowing fan 813 may protrude on sides of the air conditioning module cases 811, 812. When the blowing fan 813 is driven, the blowing fan 813 sucks air introduced into the air conditioning module coupling part 413 through the second air inlet 415 at a front surface to blow the air to a bottom end so that air may be blown to the blower out module 800.

The fan motors 814 may be disposed at outsides of the air conditioning module cases 811, 812 to be coupled with the air conditioning module cases 811, 812, and a rotation axis of the fan motor 814 may be coupled with a rotation axis of the blowing fan 813 through a coupler.

The heater 815 may include a PTC heater to generate heat by electric energy and may be disposed at a lower side of the blowing fan 813. When the heater 815 is operated, air blown from the blowing fan 813 is heated by the heater 815 to be converted into hot air, and the hot air is blown into the blower out module 800. The heater 815 may be longitudinally formed in an axial direction of the blowing fan 813 and may be disposed at the blowing fan 813 in parallel. The heater 815 may be inserted and mounted in the air conditioning module cases 811, 812 through a hole formed at one sides of the air conditioning module cases 811, 812. One end of the heater 815 in which a power terminal is disposed protrudes to outsides of the air conditioning module cases 811, 812.

An elastic support protrusion 411A for elastically supporting an end of the heater 815 inserted into the air conditioning module cases 811, 812 outward is formed at a rear surface of the front side 411 of the outer case 410 of the sterilizing module 400. Accordingly, the heater 815 may be inserted into the air conditioning module cases 811, 812, and may be elastically supported by the elastic support protrusion 411A without being locked through a locking member such as a screw to maintain a state mounted in the air conditioning module cases 811, 812.

Figure 13:
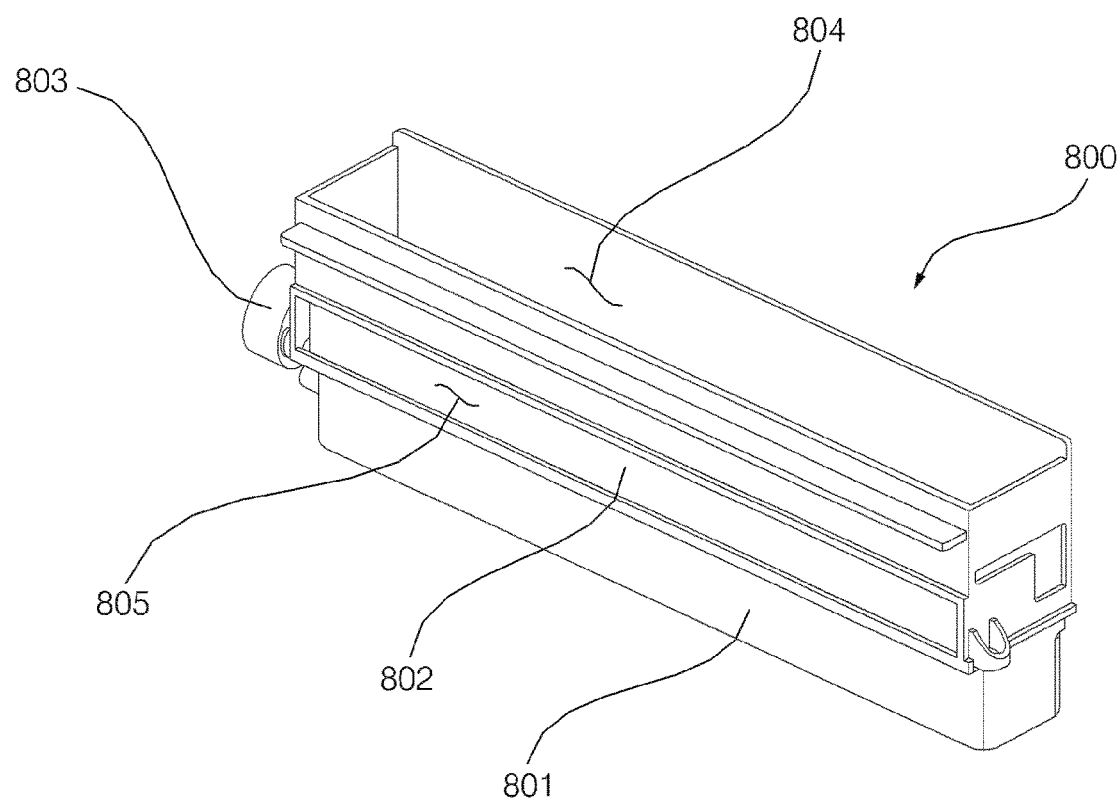
FIG. 13 is a front perspective view illustrating a blower out module shown in FIG. 12.
Figure 14:
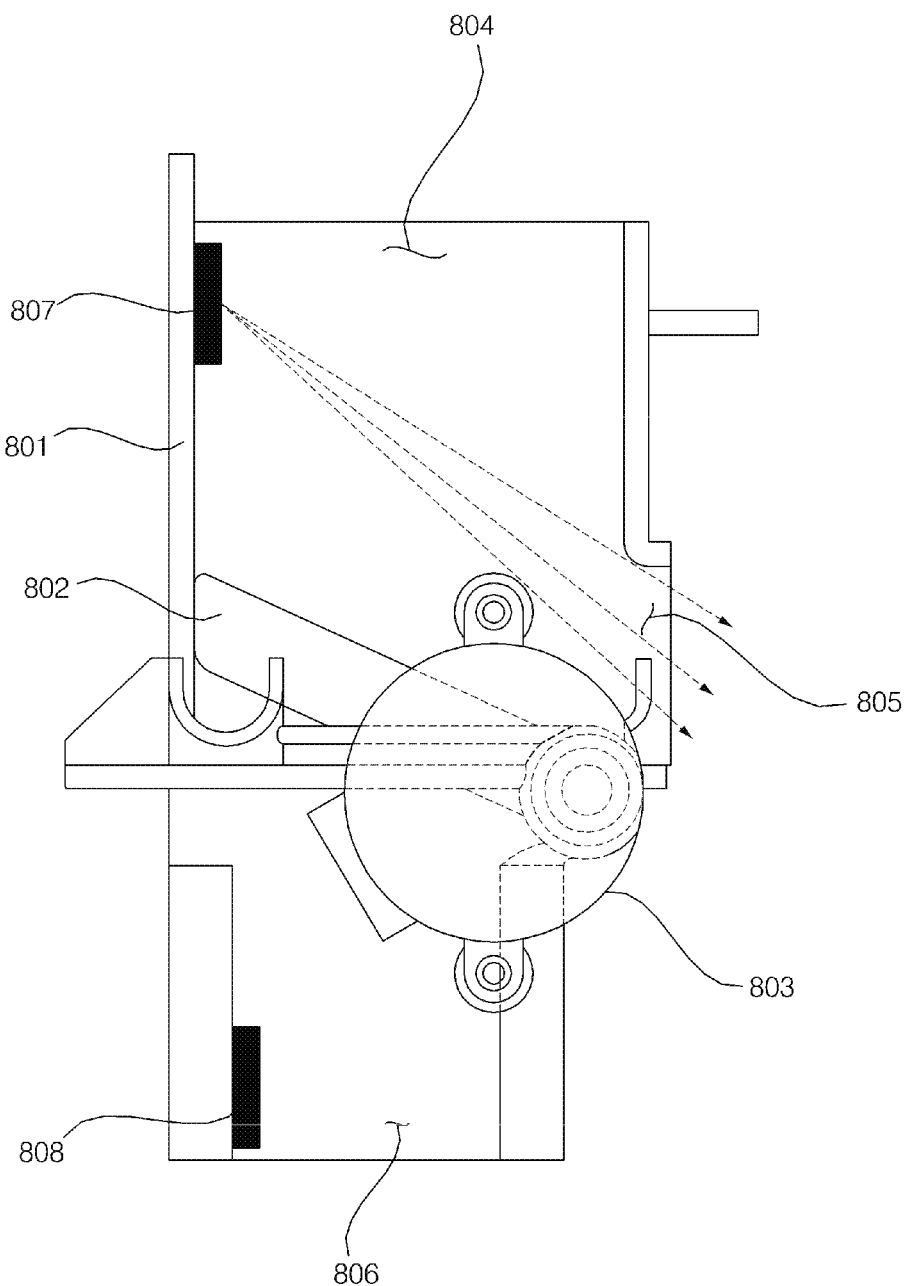
FIG. 14 is a side sectional view illustrating a blower out module shown in FIG. 12 where a front opening portion is open and a lower opening portion is shielded.
Figure 15:
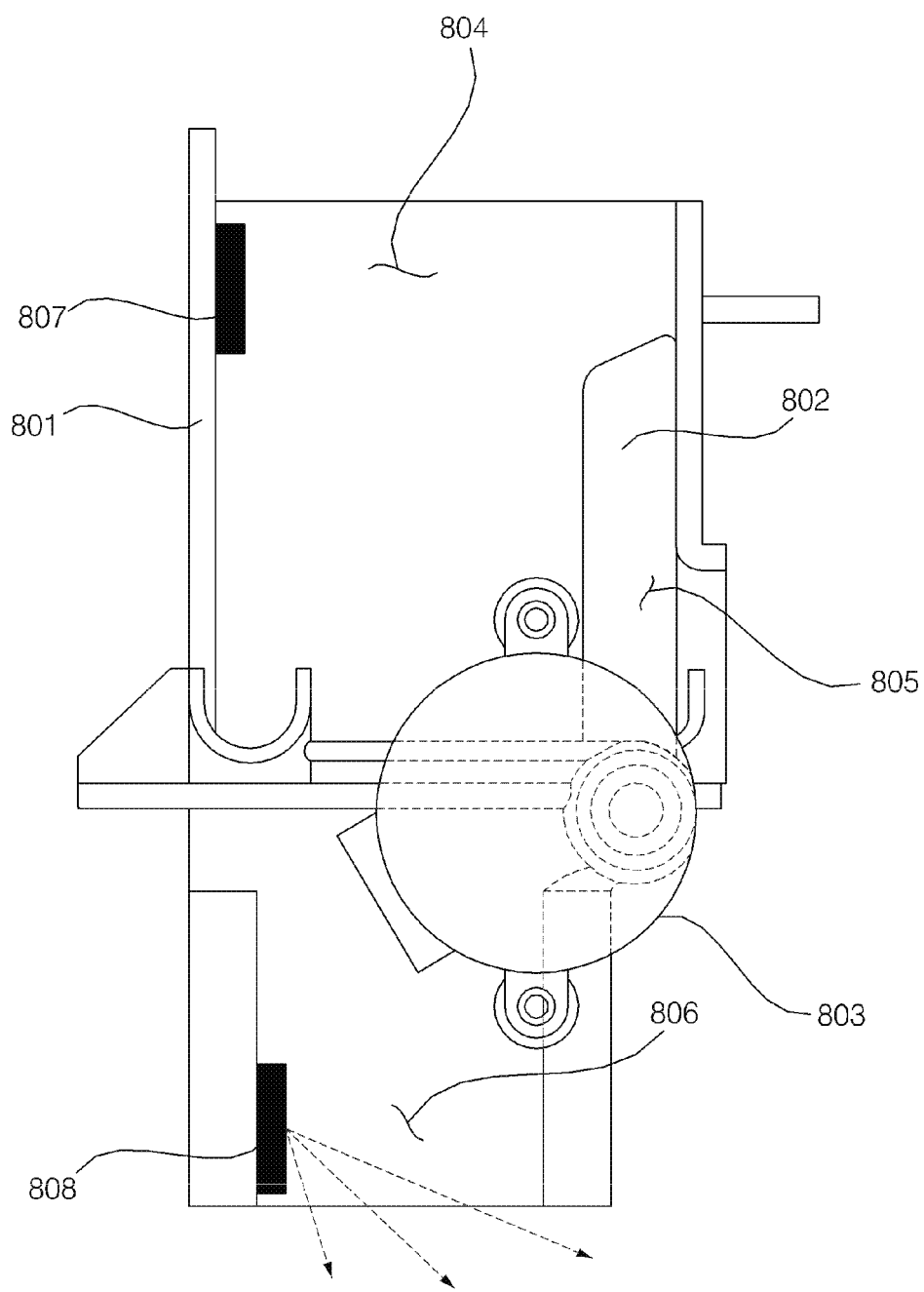
FIG. 15 is a side sectional view illustrating a blower out module shown in FIG. 12 where a front opening portion is shielded and a lower opening portion is open.

FIG. 13 is a front perspective view illustrating a blower out module shown in FIG. 12, FIG. 14 is a side sectional view illustrating a blower out module shown in FIG. 12 where a front opening portion is open and a lower opening portion is shielded, and FIG. 15 is a side sectional view illustrating a blower out module shown in FIG. 12 where a front opening portion is shielded and a lower opening portion is open.

A blower out module 800 (or blower module, vane assembly) may include a blower out module case 801, a fluid path switch vane 802 rotatably disposed inside the blower out module case 801, and a vane motor 803 configured to rotate the fluid path switch vane 802.

An open top opening portion 804 (or opening, inlet) may be formed at a top end of the blower out module case 801. An open front opening portion 805 (or opening, outlet) may be formed at a front end of the blower out module case 801. An open bottom opening portion 806 (or opening, outlet) may be formed at a bottom end of the blower out module case 801. When the top end of the blower out module case 801 is inserted into a second opening portion 219 formed at a lower frame 212 forming a bottom surface of the frame 200 to be connected with bottom ends of the air conditioning module cases 811, 812, the top opening portion 804 may communicate with the air conditioning module 810. Further, when the bottom end of the blower out module case 801 is inserted into a third opening portion 161 formed at the control panel 160 to be connected with a blower louver 181, the bottom opening portion 806 may communicate with the second air outlet 121. Moreover, the front opening portion 805 may communicate with the first air outlet 2.

The fluid path switch vane 802 may be longitudinally formed rightward and leftward to be rotatably coupled with both sides of the blower out module case 801. Rotation axes rotatably coupled with the blower out module case 801 may be formed at both ends of the fluid path switch vane 802. The vane motor 803 may be disposed at an outer side of the blower out module case 801 so that a rotating axis is coupled with a rotation axis formed at one end of the fluid path switch vane 802.

The fluid path switch vane 802 may be rotated by a driving force of the vane motor 803 to switch the flow of an air introduced from the air conditioning module 810 through a top opening portion 804 to one of the front opening portion 805 and a bottom opening portion 806. The fluid path switch vane 802 may be rotated by a driving force of the vane motor 803. When the fluid path switch vane 802 opens the front opening portion 805 and closes a bottom opening portion 806, an air sucked from the air conditioning module 810 passes through the front opening portion 805 to be discharged into a bathroom through the first air outlet 2 (e.g., airflow forward). When the fluid path switch vane 802 closes the front opening portion 805 and opens the bottom opening portion 806, an air sucked from the air conditioning module 810 passes through the blower louver 181 to be discharged into the bathroom through the second air outlet 121 (e.g., airflow downward).

The user may control a rotation position of the fluid path switch vane 802 of the blower out module 800 by operating the input unit installed at the control panel 160 to discharge the air into the bathroom through the first air outlet 2 or discharge the air into the bathroom through the second air outlet 121. The air discharged into the bathroom through the first air outlet 2 may be used to dry a user's body and the air discharged into the bathroom through the second air outlet 121 may be used to dry an inside of the bathroom.

Meanwhile, a first light source 807 and a second light source 808 may be installed in the blower out module case 801. Each of the first light source 807 and the second light source 808 may include a light emitting diode (LED). When the fluid path switch vane 802 opens the front opening portion 805, the first light source 807 is turned-on to irradiate light to the front opening portion 805. When the fluid path switch vane 802 opens the bottom opening portion 806, the second light source 808 is turned-on to irradiate light to the bottom opening portion 805.

Accordingly, when the fluid path switch vane 802 opens the front opening portion 805 and closes the bottom opening portion 806, since air blown from the air conditioning module 810 is discharged into the first air outlet 2 through the front opening portion 805 and light created from the first light source 807 is distributed through the front opening portion 805, the user may visually recognize that the air is discharged through the first air outlet 2. Moreover, when the fluid path switch vane 802 closes the front opening portion 805 and opens the bottom opening portion 806, since air blown from the air conditioning module 810 is discharged into the second air outlet 121 through the bottom opening portion 806 and light created from the second light source 808 is distributed through the bottom opening portion 806, the user may visually recognize that the air is discharged through the second air outlet 121.

According to the bathroom management apparatus of the present disclosure, in order to enable a user to quickly dry off after a shower, air may be discharged through the first air outlet 2. In order to dry the bathroom, function to dry the bathroom may be selected by discharging air through the second air outlet 121.

In addition, when the air is discharged through the first air outlet 2, light of the first light source 807 may be softly irradiated through a front opening portion 805. Light of the second light source 808 may be softly irradiated through a bottom opening portion 806 when air is discharged through the second air outlet 121. Accordingly, when the light of the first light source 807 is softly irradiated through the front opening portion 805, the user may recognize that a current mode is a mode for drying the user's body. When the light of the second light source 808 is softly irradiated through the bottom opening portion 806, the user may recognize that the current mode is a mode for drying the bathroom.

A first objective of the present disclosure provides a bathroom management apparatus capable of selecting dry of the user's body and dry of the bathroom.

A second objective of the present disclosure provides a bathroom management apparatus which allows a user to visually recognize whether the bathroom management apparatus is in a mode for drying a user's body by virtualizing a wind direction or in a mode for drying a bathroom.

According to an aspect of the present disclosure, there is provided a bathroom management apparatus which may include: a cabinet of which a front surface is open; a frame installed at an inner side of the cabinet to reinforce stiffness of the cabinet, and of which a lower side is spaced apart from the cabinet; a function module including at least one of a towel care module, a sterilizing module, a secret box module, a refrigerating module, and a charging module and mounted inside the frame; an air conditioning module coupled with the function module and disposed inside the frame; a blower out module disposed between the cabinet and a lower side of the frame, wherein first air outlet for discharging air forward is formed between the cabinet and the lower side of the frame, and a second air outlet is formed at a lower side of the cabinet, the air conditioning module sucks and blows air inside the cabinet to the blower out module, and the blower out module switches a flow of the air blown from the air conditioning module to one of the first air outlet and the second air outlet.

The blower out module may further include: a first light source installed in the blower out module case, and being turned-on when the front opening portion is open to irradiate light to the front opening portion; and a second light source installed in the blower out module case, and being turned-on when the bottom opening portion is open to irradiate the light to the bottom opening portion.

According to the first objective of the present disclosure, in order to dry a user's body after the user showers, air is discharged through the first air outlet. In order to dry the bathroom, dry of the user's body and dry of the bathroom may be selected by discharging air through the second air outlet.

According to the first objective of the present disclosure, when the air is discharged through the first air outlet, light of the first light source is softly irradiated through a front opening portion. Since light of the second light source is softly irradiated through a bottom opening portion when air is discharged through the second air outlet. Accordingly, when the light of the first light source is softly irradiated through the front opening portion, the user may recognize that a current mode is a mode for drying the user's body. When the light of the second light source is softly irradiated through the bottom opening portion, the user may recognize that the current mode is a mode for drying the bathroom.

Those skilled in the art will appreciate that the present disclosure may be carried out in specific ways other than those set forth herein without departing from the spirit and essential characteristics of the present disclosure. The above embodiments are therefore to be construed in all aspects as illustrative and not restrictive. The scope of the disclosure should be determined by the appended claims and their legal equivalents, not by the above description, and all changes coming within the meaning and equivalency range of the appended claims are intended to be embraced therein.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present disclosure.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A bathroom management apparatus comprising:
a cabinet having an open front side;
a frame provided at an inner side of the cabinet to reinforce stiffness of the cabinet, and having a lower side that is spaced apart from a bottom of the cabinet;
a function module including at least one of a towel care module, a sterilizing module, a lock box module, a refrigerating module, and a charging module, and mounted inside the frame;
a dryer coupled with the function module and disposed inside the frame; and
a vane assembly disposed between the cabinet and a lower side of the frame, wherein
a first air outlet is provided between the cabinet and the lower side of the frame for airflow in a forward direction, and a second air outlet provided at a lower side of the cabinet for airflow in a downward direction,
the dryer generates airflow and blows air inside the cabinet to the vane assembly, and
the vane assembly switches a direction of the airflow received from the dryer to one of a first direction through the first air outlet and a second direction through the second air outlet.

2. The bathroom management apparatus of claim 1, wherein the frame includes a first mounting space, a second mounting space at a lower side of the first mounting space, and a third mounting space at a lower side of the second mounting space therein, and
wherein the dryer is coupled with the function module mounted in the third mounting space.

3. The bathroom management apparatus of claim 1, further comprising a control panel disposed between the cabinet and a lower side the frame,
wherein the vane assembly is disposed in the control panel.

4. The bathroom management apparatus of claim 3, wherein
a second opening is formed at a lower side of the frame, and
a third opening is formed at the control panel,
wherein a top end of the vane assembly is inserted into the second opening such that the vane assembly is connected with the dryer, and a bottom end of the vane assembly is inserted into the third opening portion such that the vane assembly is in communication with the second air outlet.

5. The bathroom management apparatus of claim 4, wherein a blower louver having a discharge grill is coupled with a region corresponding to the second air outlet in the cabinet, and
a bottom end of the vane assembly is connected with the blower louver.

6. The bathroom management apparatus of claim 1, wherein an outer case of the function module includes a front surface for separating a storage space for a prescribed function of the function module and a storage space of the dryer, and lateral surfaces that protrude rearward from both sides of the front surface,
a dryer coupling part having a prescribed shape in which a front surface is recessed rearward and a rear surface protrudes rearward,
a first air inlet being formed at the lateral surface, and
the dryer coupling part including a second air inlet for sucking air sucked through the first air inlet.

7. The bathroom management apparatus of claim 6, wherein first openings communicating with the first air inlet are formed at both sides of the frame.

8. The bathroom management apparatus of claim 6, wherein the second air inlets are formed at a top surface and both surfaces of the dryer coupling part.

9. The bathroom management apparatus of claim 6, wherein the dryer coupling part includes a suction grill behind the second air inlet and an inner door in front of the second air inlet.

10. The bathroom management apparatus of claim 6, wherein the dryer includes
a case coupled with the dryer coupling part to communicate with the second air inlet,
a blowing fan rotatably disposed in the case,
a fan motor configured to rotate the blowing fan, and
a heater disposed in the case to heat air blown from the blowing fan.

11. The bathroom management apparatus of claim 10, wherein an elastic support protrusion that elastically supports an end of the heater inserted into the case at an outer side of the case is formed at a rear surface of the front surface.

12. The bathroom management apparatus of claim 1, wherein the vane assembly includes
a vane assembly case including a top opening in communication with the dryer, a front opening in communication with the first air outlet, and a bottom opening in communication with the second air outlet;
a fluid path switch vane rotatably disposed in the vane assembly case to switch the direction of airflow introduced through the top opening to one of the front opening and the bottom opening; and
a vane motor configured to rotate the fluid path switch vane.

13. The bathroom management apparatus of claim 12, wherein the vane assembly includes
a first light source installed in the vane assembly case, and configured to be turned-on when the front opening portion is open to irradiate light to the front opening portion; and
a second light source installed in the vane assembly case, and configured to be turned-on when the bottom opening portion is open to irradiate the light to the bottom opening portion.

14. The bathroom management apparatus of claim 12, wherein the vane assembly has a housing having a front wall and a rear wall that form a cavity inside the housing, and the fluid path switch vane is mounted inside the cavity such that a rotational axis is provided toward the front wall.

15. The bathroom management apparatus of claim 14, wherein the front opening is provided on the front wall and the bottom opening is provided to extend between the front wall and the rear wall.

16. The bathroom management apparatus of claim 15, wherein a first distal end of the fluid path switch vane is provided at the rotational axis and a second distal end of the fluid path switch vane rotates relative to the rotational axis.

17. The bathroom management apparatus of claim 16, wherein when the vane motor is controlled to rotate the fluid path switch vane for airflow through the first air outlet, the fluid path switch vane rotates such that the second distal end contacts an inner surface of the rear wall, and when the vane motor is controlled to rotate the fluid path switch vane for airflow through the first air outlet, the fluid path switch vane rotates to such that the second distal end contacts an inner surface of the front wall.

18. The bathroom management apparatus of claim 14, wherein the vane motor is mounted outside the housing of the vane assembly at a lateral wall of the housing.

* * * * *